(12) United States Patent
Adachi et al.

(10) Patent No.: US 7,509,162 B2
(45) Date of Patent: Mar. 24, 2009

(54) OPERATION ERROR DETECTION DEVICE, EQUIPMENT INCLUDING THE DEVICE, OPERATION ERROR DETECTION METHOD AND EQUIPMENT EVALUATION METHOD

(75) Inventors: Shinobu Adachi, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 11/666,911

(22) PCT Filed: Oct. 31, 2005

(86) PCT No.: PCT/JP2005/019999

§ 371 (c)(1),
(2), (4) Date: May 3, 2007

(87) PCT Pub. No.: WO2006/051709

PCT Pub. Date: May 18, 2006

(65) Prior Publication Data

US 2007/0266273 A1  Nov. 15, 2007

(30) Foreign Application Priority Data

Nov. 10, 2004 (JP) ............................. 2004-326517

(51) Int. Cl.
*A61B 5/00* (2006.01)
(52) U.S. Cl. ...................... 600/544; 600/545
(58) Field of Classification Search .................. None
See application file for complete search history.

(56) References Cited

FOREIGN PATENT DOCUMENTS

| JP | 1-230343 A | 9/1989 |
| JP | 9-326893 | 12/1997 |
| JP | 2578013 A | 5/1998 |
| JP | 2001-184139 | 7/2001 |
| JP | 3060949 | 4/2002 |

OTHER PUBLICATIONS

Samuel Inverso, "Automatic Error Recovery Using P3 Response Verification for a Brain-Computer Interface," Jul. 20, 2004, Rochester Institute of Technologu Computer Science Department.*
Nishi, Daishi et al., "Jisho Kanren Den'i o Mochiita Kioku ni Kansuru Kisoteki Kenkyu", ("The study on recent memory using event-related potentials"), The Institute of Electronics, Information and Communication Engineers Gijutsu Kenkyu Hokoku, vol. 100, No. 598, Jan. 19, 2001, pp. 17 to 24.
"Guideline Proposal of Evoked Potential Measurement," revised in 1997 and a partial English translation thereof.

* cited by examiner

*Primary Examiner*—Robert L Nasser
(74) *Attorney, Agent, or Firm*—Dickey & Pierce, P.L.C.

(57) ABSTRACT

An input section (101) receives a manipulation input of a user (50). A biological signal detection section (102) measures an event-related potential of electroencephalogram of the user (50). An operation error judgment section (103) judges using the event-related potential of the electroencephalogram of the user (50) at around 300 ms from a timing when the input section (101) receives the manipulation input as a starting point whether or not the manipulation input is due to an operation error of the user. An equipment operation control section (104) determines an operation of an equipment (1) based on a result of judgment by the operation error judgment section (103).

10 Claims, 19 Drawing Sheets

FIG. 9

| Input | Correction answer |
|---|---|
| abouta | about a |
| acn | can |
| differnt | different |
| hge | he |
| ytou | you |
| Helle | Hello |

FIG. 13

Known evaluation method

| Operation button | Percentage of mistake |
|---|---|
| A | 20% |
| B | 20% |
| C | 40% |
| D | 10% |

FIG. 14

Operability evaluation method using operation error detection device

| Operation button | Percentage of mistake | Percentage of operation error |
|---|---|---|
| A | 20% | 2% |
| B | 20% | 18% |
| C | 40% | 5% |
| D | 10% | 0% |

Subject A
Operation error = 15

Average of sum for 6 subjects
Operation error = 9

OPERATION ERROR DETECTION DEVICE, EQUIPMENT INCLUDING THE DEVICE, OPERATION ERROR DETECTION METHOD AND EQUIPMENT EVALUATION METHOD

TECHNICAL FIELD

The present invention relates to a device for providing some services and information to a user of an information terminal or the like, and more particularly relates to a technique for detecting an operation error of a user when the user operates an equipment and providing more suitable service to the user based on a result of the operation error detection.

BACKGROUND ART

In recent years, equipments for information terminals and the like have been highly developed and, accordingly, it has been more and more difficult to manipulate such a highly developed equipment. For example, the number of manipulation buttons is increased and a density is increased, so that an "operation error", i.e., an error of mistakenly pressing a manipulation button by a user easily happens. Also, in order to complete an operation within a limited time, a user is required to complete manipulation in a short time in many situations and, therefore, an operation error such as mistakenly pressing a button inevitably occurs.

To eliminate such operation errors, modification of interface design such as changes of GUI, adjustment of button position and the like has been conventionally examined. For example, in Patent Reference 1, an equipment including an All Clear button for resetting a function which has been set to an initial state is disclosed. In the equipment, when the All Clear function is instructed, a display for confirming whether or not the All Clear function may be executed appears and, after a confirmation instruction is received, the All Clear function is executed. Referring to Patent Reference 2, in a car navigation system with which both of an audio compact disk and a map storage compact disk can be used, when a map storage compact disk is loaded in the car navigation system and a user performs an eject manipulation of the compact disk, a display for operation. confirmation is performed.

In the above-described examples, for an operation which largely changes performance of an equipment, such as All Clear of setting function (Patent Reference 1), ejection of a map storage compact disk (Patent Reference 2) and the like, which makes map display impossible, confirmation of a user for an operation instruction is requested and only if confirmation is obtained, the function is executed.

In the same manner, in operation of computer, before an irreversible, important operation such as deletion of a file, format of a hard disk and the like is performed, a confirmation display appears for selecting Yes or No.

Unlike the above-described example where an operation of confirming user's intention for such an important operation is requested, there is another example, a state of a user is recognized by measuring a biological signal of the user. In Patent Reference 3, at an interface of computer or the like, the degree of fatigue of a user is judged from a heart rate, myoelectric potential, the degree of sweating and the like. When the user is fatigue, a screen display is enlarged, contrast is emphasized, sound is turned to louder, or an input sensitivity of an input device such as a mouse and a pen tablet is increased. Thus, it is believed that the degree of fatigue of the user can be reduced and, as a secondary effect, reduction in operation error can be expected.

Patent Reference 1: Japanese Patent No. 3060949
Patent Reference 2: Japanese Utility Model No. 2578013
Patent Reference 3: Japanese Laid-Open Publication No. 2001-184139

DISCLOSURE OF THE INVENTION

Problems that the Invention is to Solve

However, as shown in Patent Reference 1 and Patent Reference 2, an operation of user's confirmation which is performed immediately before execution of an important function forces a user to perform mandatory confirmation operation for each time. In addition, since confirmation operation is required many times, confirmation operation itself is executed as part of a series of procedures in user's operation and confirmation becomes less effective. Therefore, for example, when a user operates computer, the user might almost mechanically select an icon of "Yes" in response to a confirmation message and perform an important operation even when the user does not want to perform.

In Patent Reference 3, an additional operation by a user is not required. The degree of fatigue of a user is directly measured by biometric measurement, and then an interface is modified to reduce the fatigue of the user. However, whether or not designing interface so as to enlarge screen display of a display device and the like can reduce operation errors themselves, and it is not possible to completely eliminate operation errors.

As described above, techniques for preventing operation errors have been proposed, but there have not been proposed techniques for directly detecting an operation error of a user and dealing with the detected error.

It is therefore an object of the present invention to directly detect an operation error of an equipment made by a user and avoid the generation of unintentional equipment operation.

Solution to the Problems

The present inventors have newly developed a method in which a state of an operation error generated when a user executes an unintentional operation is directly detected using a biological signal, specifically, an event-related potential which is measurable by electroencephalograph. Using a result of detection of an operation error, a equipment response is corrected, thereby markedly improving usability of the equipment.

Herein, correction of the equipment response includes executing an equipment operation only when an operation error is not detected, canceling a last operation before detection of an operation error, notifying a user that an equipment has recognized an operation error, estimating what input the user really wanted to make when an operation error happened and automatically correcting the operation error, and the like.

Specifically, according to the present invention, as operation error detection, a manipulation input of a user is received, an event-related potential of electroencephalogram of a user is measured and then, using the event-related potential at around 300 ms after a timing of receiving the manipulation input as a starting point, whether or not the manipulation input is due to an operation error of the user is judged. Therefore, an operation error of a user can be directly detected.

Moreover, an equipment according to the present invention, as an equipment for performing the above-described operation error detection, includes an equipment operation control section for determining an operation of the equipment based on a result of operation error judgment. Thus, when an operation error of a user is detected, an equipment reaction is modified, so that usability of the equipment is improved.

In the equipment of the present invention, when it is judged that a manipulation input is due to an operation error, it is preferable to stop sending the manipulation input to the equipment operation control section. Thus, an irreversible operation of the equipment which is to be generated due to an operation error of a user can be automatically prevented before happening, so that reliability of the equipment under operation is increased.

In the equipment of the present invention, when it is judged that a manipulation input is due to an operation error, it is preferable that the equipment operation control section cancels an operation according to the manipulation input. Thus, it is no longer necessary to force a user to perform a bothering correction operation and user friendliness of the equipment is largely improved.

In the equipment of the present invention, when it is judged that a manipulation input is due to an operation error, it is preferable that a correction operation is determined for the manipulation input and the correction operation is sent to the equipment operation control section. Thus, a user does not have to perform correction for the operation error, so that user friendliness is largely improved.

In the equipment of the present invention, when it is judged that a manipulation input is due to an operation error, it is preferable that the equipment operation control section notifies a user that the operation error has been detected. Thus, it is possible to feed back to the user that the equipment has detected an operation error of the user, so that the user can recognize whether or not the equipment has automatically corrected the operation error, whether or not an instruction of the user has been cancelled and the like.

An equipment according to the present invention, as an equipment for performing the above-described operation error detection, may include a storage section for storing a manipulation input and an operation error judgment result. Thus, more detail usability evaluation becomes possible.

Effects of the Invention

According to the present invention, an operation error of a user can be directly detected based on an event-related potential of an electroencephalogram of a user. By application of the detection to modification of an equipment reaction, usability of an equipment is markedly improved.

BRIEF DESCRIPTION OF THE DRAWINGS

FIG. 9 is a table showing exemplary data stored in a correction answer estimation rule database.

FIG. 13 is a table showing an example of results of operability evaluation by a known evaluation method.

FIG. 14 is a table showing an example of results of operability evaluation according to the fourth embodiment of the present invention.

Figure 1:
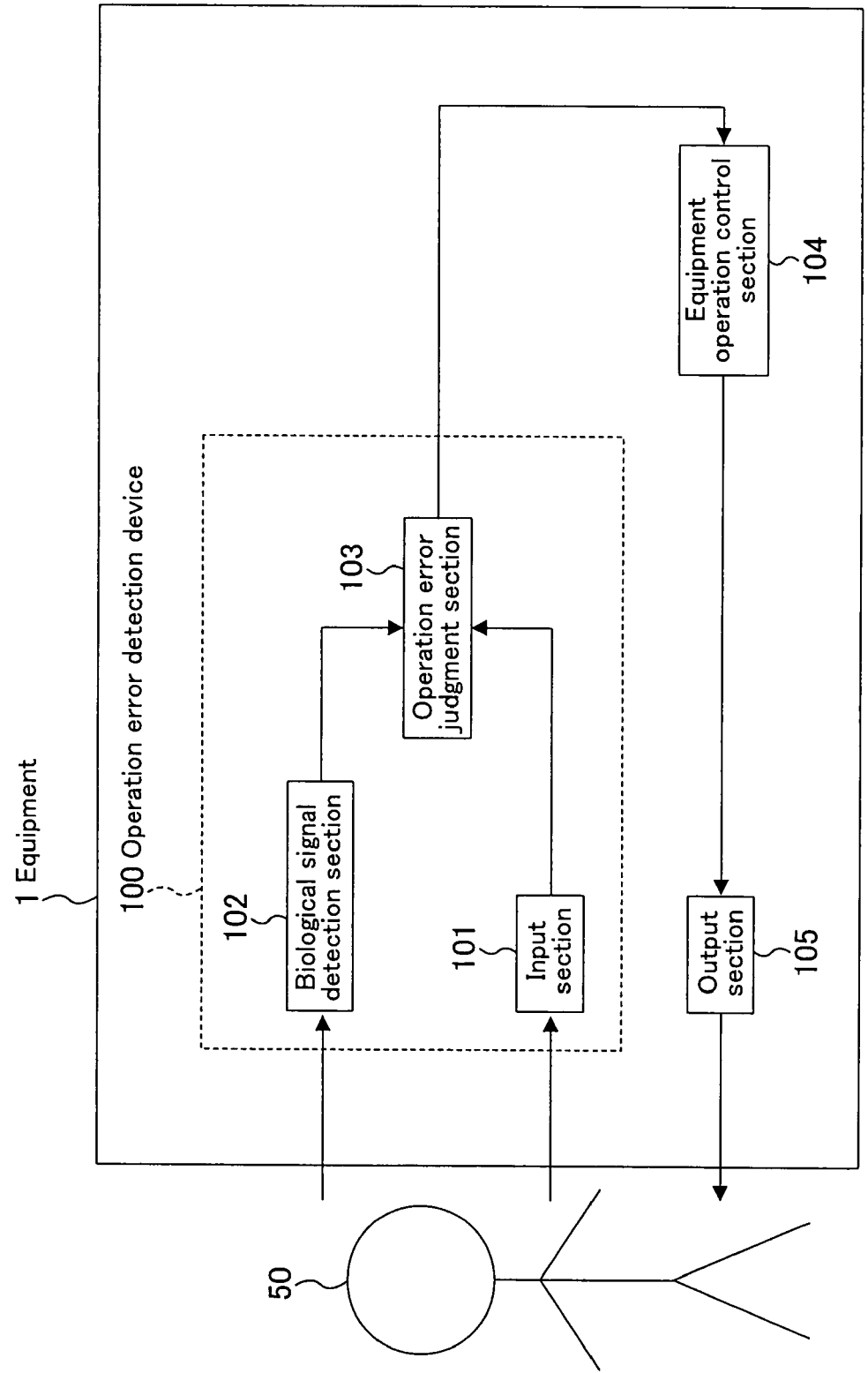
FIG. 1 is a block diagram illustrating a configuration of an equipment including an operation error detection device according to a first embodiment of the present invention.

EXPLANATION OF REFERENCE NUMERALS 1, 2, 3, 4 and 20 Equipment
30 Correction operation determination section
50 User
100, 200 Operation-error detection device
101 Input section
102 Biological signal detection section
103 Operation error judgment section
104 Equipment operation control section
105 Output section
10A Processing mode changing section
306 Correction operation estimation section
307 Correction answer estimation rule database
408 Evaluation result storage database (storage section)

BEST MODE FOR CARRYING OUT THE INVENTION

First, how the present inventors have reached the present invention will be described. Before that, to clearly show what operation error is subjected according to the present invention, different cases where a user can not correctly operate an equipment are assorted. There are two states where a user can not correctly operate an equipment, i.e., A) a case where although a user assumes a correct operation and is trying to perform the correct operation, the user performs a wrong manipulation and thus an unexpected result is obtained; and B) a case where because a model of an operation which the user thought of is not correct, an assumed manipulation is performed in a right manner but an unexpected result is obtained.

The above-described two cases are common in terms that an equipment operation that a user does not expect is performed. However, when users' thinking processes are compared to one another, there is a big difference between the two cases. In A), an operation error is made because of a problem of handleability or a mistake made by a user in performing operation. In B), as an operation model of an equipment that a user thinks of is not correct, a correct manipulation for an equipment operation is not assumed. Hereafter, to distinguish the two cases, the A) type is referred to as an "operation error" type. The case of B) is a "disappointment" type since an actual tool operation is different from an equipment operation that a user expects.

An object of the present invention is to directly measure an operation error of the A) type and improve handleability of an equipment based on detection of an operation error.

When a user performs an operation error, the user often notices his/her own operation error, mumbling, "Oh no!" or "I made a mistake!" The present inventors newly found that in such a state, a signal which can be characteristically observed by electroencephalograph is generated. If this signal is used, direct detection of an operation error which has been conventionally impossible can be performed. Use of this operation error signal makes it possible to prevent a function that a user does not intend from being executed in response to an operation error without requesting confirmation operation to the user.

Next, it will be described that the above-described operation error signal can be detected.

First, an experiment for detecting an operation error, which the present inventors have conducted under the assumption that a user operates an equipment, will be described.

Figure 15:
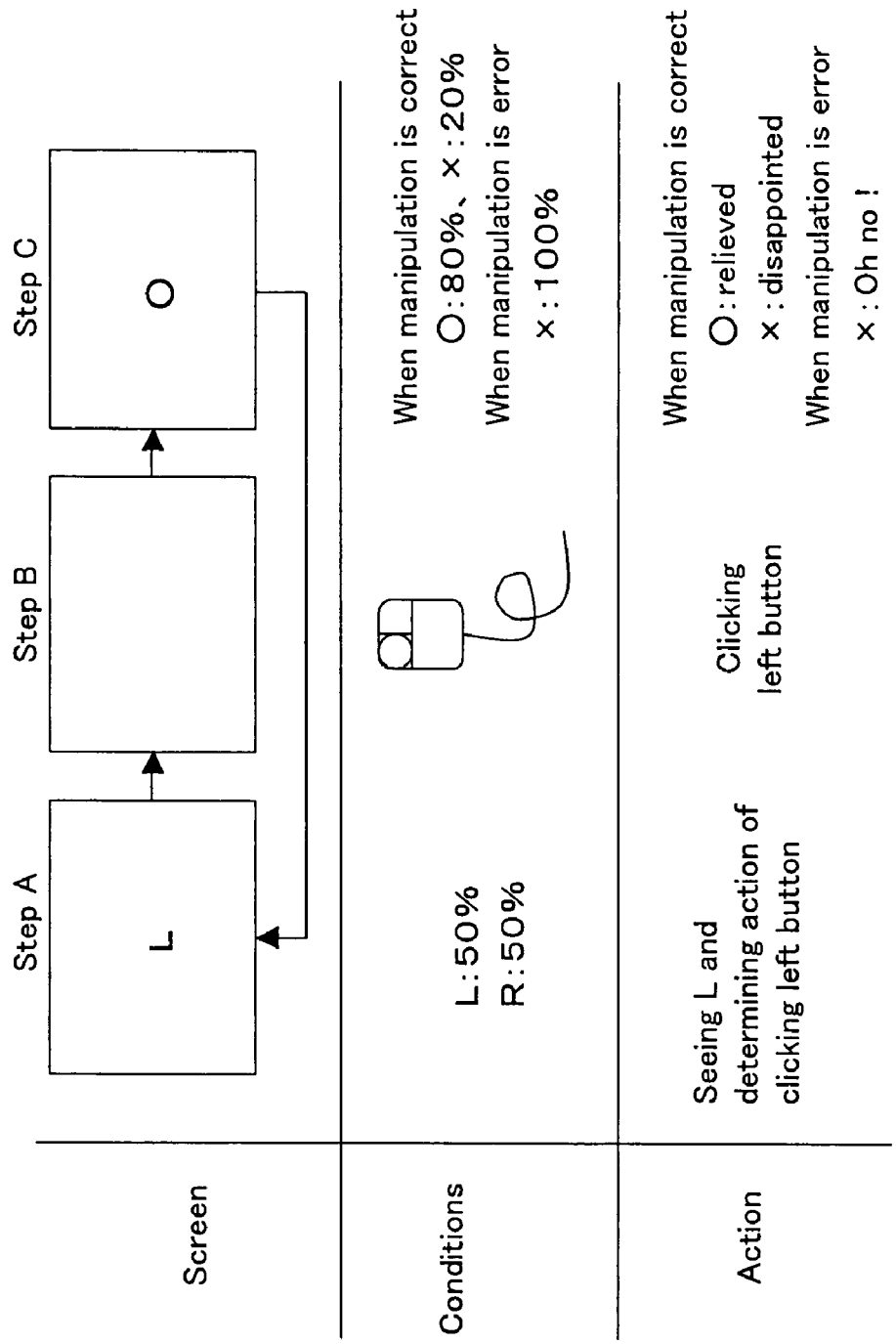
FIG. 15 is an illustration showing a brief procedure of an experiment conducted by the present inventors.

FIG. 15 is an illustration showing a brief procedure of the experiment. This experiment is composed of sequential steps of: providing an instruction to a subject (Step A); in response to the instruction, allowing the subject to think about necessary action and to manipulate an equipment (Step B); and presenting an equipment operation to the subject as a result of the subject's manipulation (Step C).

First, an experiment executer explains to a subject "When a letter 'L' or 'R' is displayed in the screen, please click the left button of a mouse for the letter 'L' or click the right button of the mouse for the letter 'R'." Then, "L" or "R" is selected at random at a probability of 50% and is displayed on the screen (Step A). The subject looks at the displayed letter and clicks the right or left button according to the directed rule (Step B). In response to the subject's manipulation, whether or not the correct button has been clicked is displayed as "o" symbol (indicating a correct answer) or "x" symbol (indicating an incorrect answer) on the screen (Step C).

In this experiment, for example, if although "L" is displayed, the subject clicks the right button by mistake and think "Oh no!", this case is considered to be an operation error state.

In this experiment, even when a correct button is clicked, "x" is displayed at a probability of 20%. When "x" is displayed, the subject, who is expecting that "o" will be displayed because of correct clicking, might think "Why?" Namely, the subject falls in a "disappointment" state in which the equipment operates differently from his/her expectation.

Figure 16:
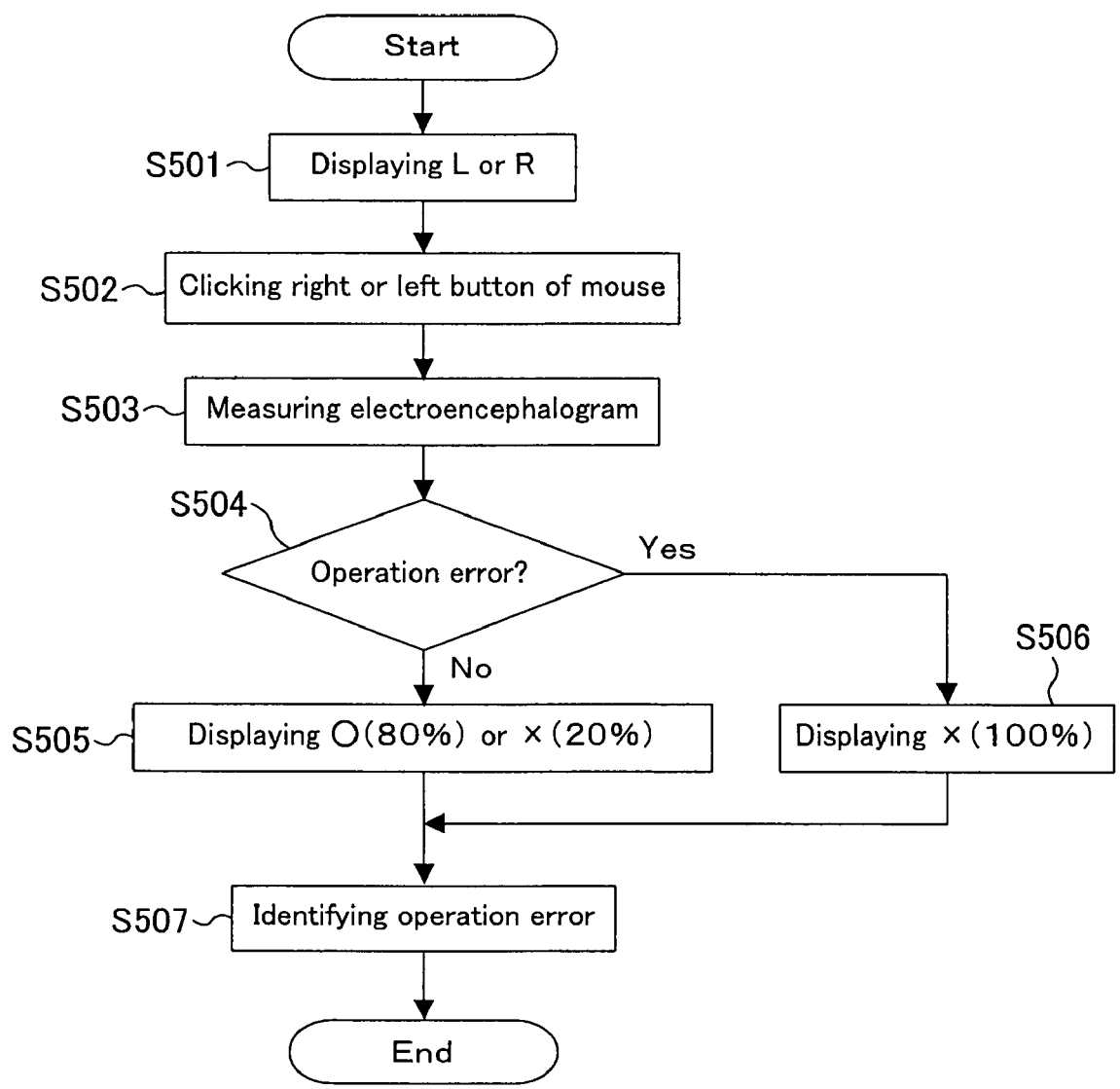
FIG. 16 is a flowchart showing a procedure for one trial of the experiment.

FIG. 16 is a flowchart showing a procedure for one trial. First, the letter "L" or "R" is selected at a probability of 50% and is displayed on the screen (S501), the subject looks at the screen, selects which button is to be clicked, and manipulates the mouse (S502). The event-related potential in the electroencephalogram of the subject is measured from the timing, as a starting point, when the mouse is clicked (S503). The electroencephalogram is recorded continuously during the experiment and data in a necessary interval can be selected and processed. As for the event-related potential, an interval for which measurement has to be performed may be set to be a range from the timing of the mouse click to around 1000 ms after the mouse click. In response to the subject's manipulation, whether or not the mouse is correctly operated is judged (S504). If it is judged that the mouse is correctly operated (No in S504), right after the subject's manipulation, "o" is displayed at a probability of 80% and "x" is displayed at a probability of 20% (S505). Moreover, if it is judged that the mouse is not correctly operated (Yes in S504), "x" is displayed at a probability of 100% (S506). Then, the event-related potential measured (S503) from the timing, as a starting point, when the mouse is manipulated is processed to identify an operation error signal (S507).

In the experiment, to a plurality of subjects, a trial in which "o" is to be displayed every time was carried out 30 times as practice first, and then, the trial through the procedure shown in FIG. 16 was carried out 100 times.

Figure 17B:
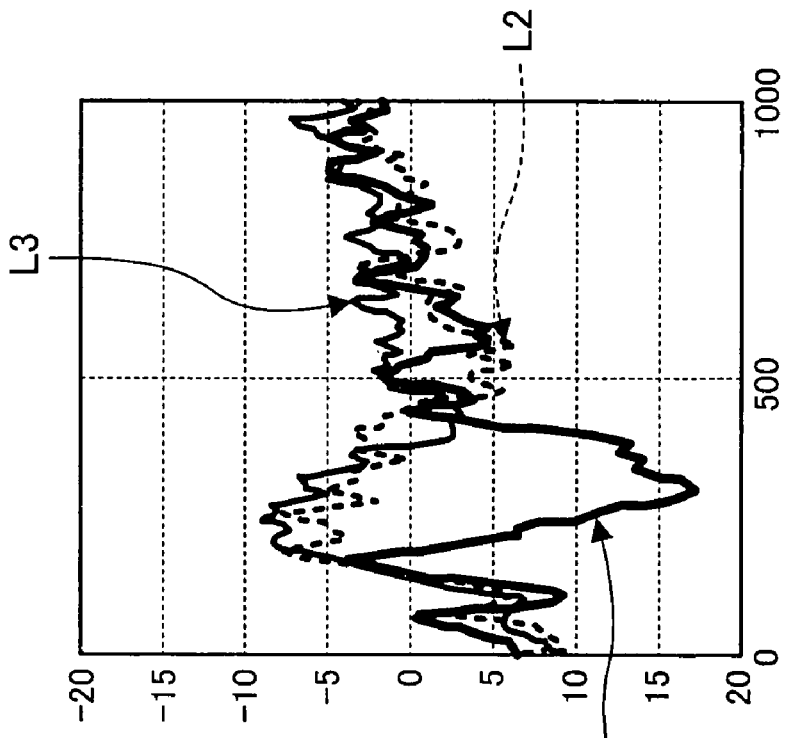
FIG. 17(b) is a graph showing experiment data obtained summing up operation errors of a subject A.
Figure 17A:
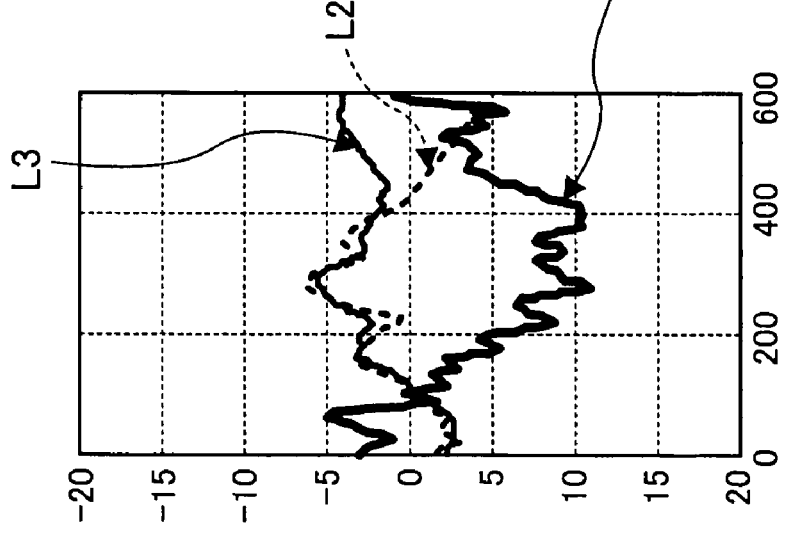
FIG. 17(a) is a graph obtained by summing up all operation error signals of 6 subjects.

FIG. 17 shows the experiment results. FIG. 17(a) is a graph obtained by summing up all operation error signals of 6 subjects. FIG. 17(b) is a graph obtained by summing up operation error signals of a subject A, who made the largest number of operation errors in 15 trials among other subjects than the 6 subjects. Each of the graphs of FIGS. 17(a) and 17(b) was obtained by averaging out potential waveforms measured by an electroencephalograph. In each of FIGS. 17(a) and 17(b), the abscissa indicates the time (ms) which has lapsed since a mouse click and the ordinate indicates potential ($\mu$V). Each of FIGS. 17(a) and 17(b) includes three waveforms. A waveform L1 is a waveform obtained when an "operation error" occurred, i.e., when although a correct action was assumed, the correct action was not executed due to an operation error and "x" was displayed. A waveform L2 is a waveform obtained when a "disappointment" occurred, i.e., when although a correct action was performed, "x" was displayed and an assumed result was not obtained. The "operation error" L1 and the "disappointment" L2 indicate quite different waveforms from each other even though both were the cases where "x" was displayed. This implies that those are results of different processes in the brain.

Note that four electrodes 1) Pz, 2) and 3) A1 and A2, and 4) body earth (Z) were attached to a median vertex; respective ears, and a root of nose, respectively, according to the international 10-20 system. The sampling frequency was set to be 1000 Hz.

It is understood from each of FIGS. 17(a) and 17(b) that when an operation error occurs, an event-related potential having a different characteristic from that of a potential of a normal course which appears around about 300 ms after a mouse click. Namely it is expected that measurement of the event-related potential leads to detection of a case where a user has performed an operation error and though "Oh no!"

As shown in Minoru Shimokouchi, *Draft guideline for evoked potential measurement*, 1997 revision, p. 14, it is known that when subjects are tested using visual oddball stimulus, a latency for P3 is about 400 ms, which is about 100 ms longer than a latency in the case where subjects are tested using auditory odd ball stimulus, i.e., 300 ms. In a visual oddball stimulus experiment which has been separately conducted by the inventors, as a result of the experiment, a latency for P3 was 450 ms. Compared to the above-described cases, for a component of the event-related potential measured in the operation error detection experiment which seems to be P3, a peak appears at a relatively early time point, i.e., 300 ms. Accordingly, it is understood that the event-related potential occurred not because "x" was displayed but because the user recognized that he/she has performed an operation error immediately after his/her manipulation.

As has been clearly shown by the above-described experiment, in the experiment conducted assuming user's equipment operation states, the event-related potential measured by an electroencephalograph is clearly different between the case where an operation error has occurred and the case where an operation error has not occurred. Therefore, the event-related potential can be used as a signal indicating an "operation error" in an interface of an equipment.

(Method for Detecting Operation Error Signal)

Next, a specific example of a method for detecting an operation error signal will be described with reference to the flowchart of FIG. 18. In this method, a standard waveform (referred to as a target template) to which signals when an operation error is performed are summed up and another standard waveform (referred to as a control template) to which signals in a normal state where an operation error is not performed are summed up are generated in advance and these templates are utilized for detection of the "operation error signal."

Figure 18:
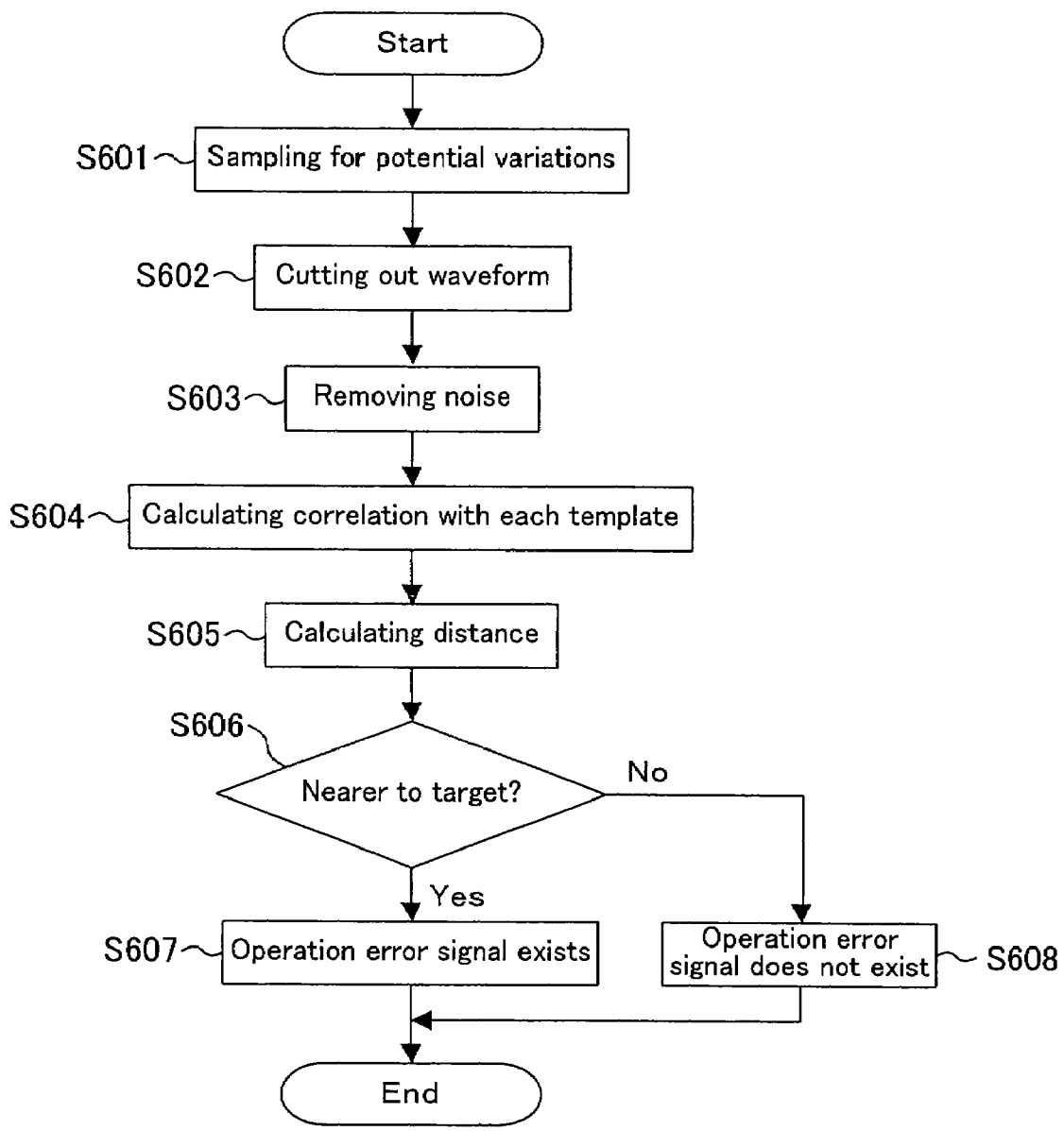
FIG. 18 is a flowchart showing a specific example of methods for detecting an operation error signal.

As shown in FIG. 18, first, potential variation in an electroencephalogram is sampled (S601) from a timing, as a starting point, when a mouse is clicked. The sampling frequency may be 200 Hz, 500 Hz, 1000 Hz, or the like, for example. Then, a waveform in a range relating to detection of the "operation error signal" is cut out from the obtained potential variation in the electroencephalogram (S602). From the results of the above described experiment, it is known that the "operation error signal" is detected at part around 300 ms after manipulation input. Further, in a relatively earlier range after the manipulation input, a waveform includes primary response to auditory stimulation or visual stimulation, and therefore, the part corresponding thereto is preferable to be removed. As such, the range between 100 ms and 500 ms after the manipulation input is cut out.

Of course, the cut out range is not limited thereto and may be set in a range between 200 ms and 400 ms, between 100 ms and 700 ms, or the like. Alternatively, a range within approximately 1 second after the manipulation input may be cut out with no early limit set.

Next, noise is removed from the cut out waveform (S603). Herein, high-frequency components mixed with the signal is cut, the signal is allowed to pass through a low-pass filter of, for example, 40 Hz, a waveform with an amplitude of 40 μV or more is removed from an object to be identified for reducing influence of electrooculogram by a blink, or the like.

Subsequently, each correlation between the signal from which noise is removed and the signal templates of the target template and the control template is calculated (S604). This correlation calculation calculates how the signal waveform correlates with each template.

A distance between the signal waveform and each of the templates is calculated (S605). For example, Mahalanobis distance is employed for the distance calculation. This Mahalanobis distance indicates a distance from a gravity of a group taking account of variance and covariance of data. With the use of Maharanobis distance, judgment is performed as to which template the signal waveform is nearer (S606). It is known that the judgment utilizing Maharanobis distance exhibits higher recognition ability than judgment according to mere correlation magnitude.

When it is judged that the signal waveform is near the target template (YES in S606), it is recognized that the operation error signal is detected, namely, that the user thinks that he/she performed an operation error (S607). On the other hand, when it is judged that the signal waveform is near the control template (S608) not the target template, it is recognized that the operation error signal is not detected, namely, that the user thinks that an operation error was not detected and the response as expected was obtained.

Employment of the method using such templates enables detection of the operation error signal to some extent in an electroencephalogram, of which waveform includes severe variation, and accordingly, of which recognition from a single waveform is considered to be difficult.

Figures 19A, 19B:
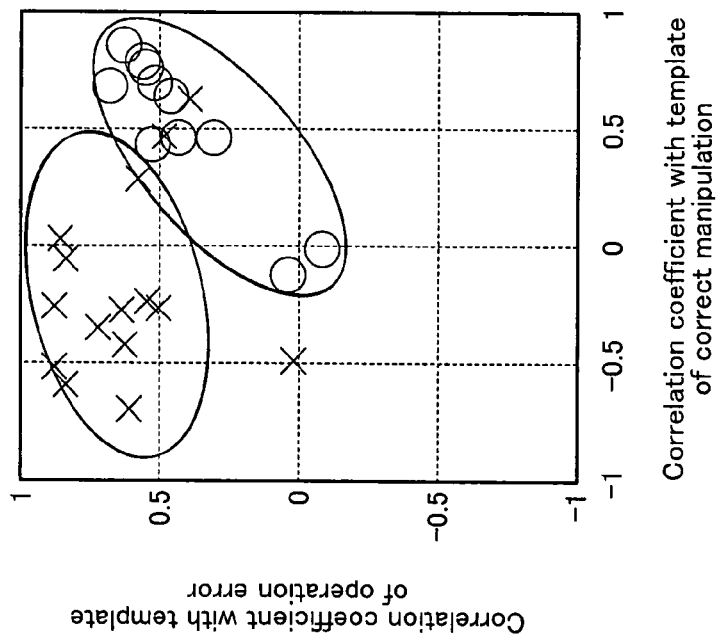
FIG. 19(a) is a graph showing correlation coefficient for each trial.
FIG. 19(b) is a table showing a result of detection of an operation error signal.

FIG. 19 is a table showing results of operation error signal detection according to the procedure shown in FIG. 18 using the aforementioned experiment data. In FIG. 19, only analysis results for the target A for which an enough number of data of operation errors were obtained are shown. FIG. 19(a) shows a graph in which the abscissa indicates the correlation coefficient with the control template (correct operation) and the ordinate indicates the correlation with the target template (operation error) and respective coordinates of waveforms are plotted. In FIG. 19(a), "o" indicates a signal at a correct operation and "x" indicates a signal at an operation error.

FIG. 19(b) is a table showing the number of operation errors of the subject A and the number of times of correct judgment. Thirteen operation error signals out of 15 operation error signals were recognized, namely, almost 90% of data was judged. In this manner, FIG. 19 shows that with the use of the method of FIG. 18, operation error signals can be recognized with quite high accuracy even though there are still variations in signal waveform.

The signal templates of the target template and the control template are used herein. However, only the target signal template may be used. For example, Maharanobis distance from the target signal template may be calculated and then may be compared with a predetermined value to judge whether or not an operation error has been performed.

As another alternative, instead of the use of the templates, for example, the potential immediately after manipulation input may be compared with the potential at about 300 ms after the manipulation input to detect an operation error signal. As can be understood from FIG. 17, whether or not an operation error has been performed, a potential related to primary response to manipulation input appears immediately after the manipulation input. Therefore, for example, difference between an average potential of time when an initial component appears and an average potential of time (around 300 ms after input) when an "operation error signal" is detected is threshold-processed to detect an operation error signal.

Figure 20:
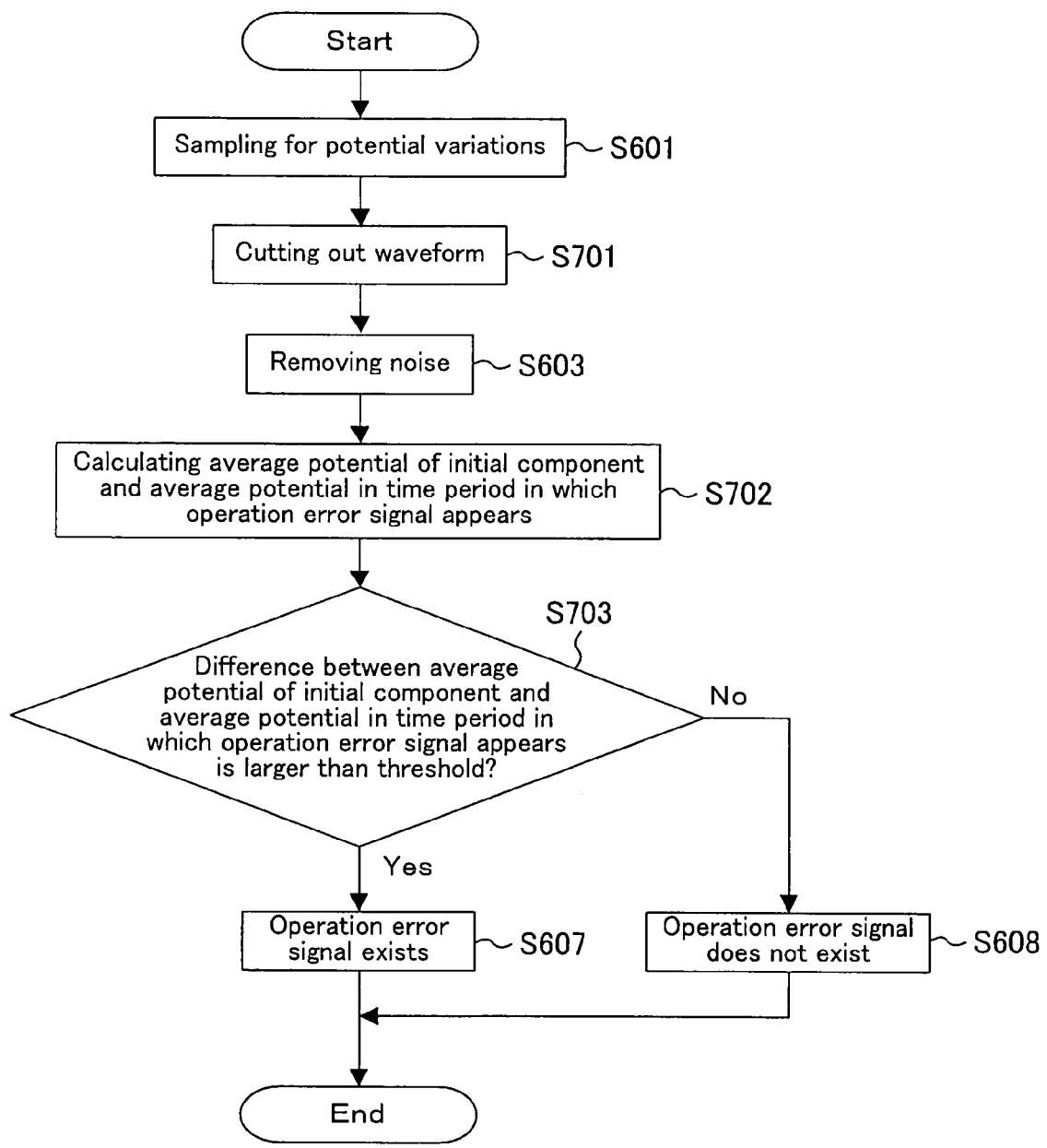
FIG. 20 is a flowchart showing another specific example of methods for detecting an operation error signal.

Now, another specific example of a method for detecting an operation error signal will be described with reference to the flowchart of FIG. 20. In FIG. 20, each step also shown in FIG. 18 is identified by the same reference numeral and therefore the description thereof will be omitted. Note that unlike the method employing the templates, templates do not have to be prepared in advance in this method.

As shown in FIG. 20, first, of potential variations in an electroencephalogram measured from a timing when a mouse is clicked as a starting point (S601), a waveform in the range from 0 ms after manipulation input to around 300 ms when an operation error signal is detected is cut out (S701).

Next, noise is removed from the cut out waveform (S603). Then, an average potential of initial component which is primary response relating to manipulation input and an average potential at around 300 ms when an "operation error signal" appears are calculated (S702). For example, a time when primary response appears and a time when an operation error signal appears are set to be in a range from 0 ms to 100 ms after manipulation input and a range from 250 ms to 350 ms after the manipulation input, respectively, and an average value of sampling data measured in each of these time frames is calculated as an average potential.

Next, the average potential of an initial component (e.g., 0 ms to 100 ms) is subtracted from the average potential of time (e.g., 250 ms to 350 ms) when an operation error signal appears to obtain a difference between the average potentials and the difference is compared with a predetermined threshold (S703). As shown in FIG. 17, an operation error signal is a positive component and therefore it is assumed that the difference between the average potentials when operation error is performed is a positive value. In this case, a threshold is set to be, for example, 10 μV and it is judged whether or not the difference between the average potentials is larger than the threshold.

When the difference between the average potentials is larger than the threshold (Yes in S703), it is judged that a positive component appears at around 300 ms after manipulation input and it is recognized that an operation error signal exists (S607). On the other hand, when the difference between the average potentials is smaller than the threshold (No in S703), it is judged that a positive component does not appear at around 300 ms after manipulation input and it is recognized that an operation error signal does not exist.

As a result of detection of operation error signals of the subject A according to the procedure shown in FIG. 20, 12 operation error signals out of 15 operation errors were correctly recognized. Influences of noise on an event-related potential at a low S/N ratio is reduced. This shows that an operation error signal can be recognized with quite high accuracy and also by a method in which an average potential in a certain period of time is calculated.

Although there is still some problem with accuracy, an operation error can be detected by merely comparing a potential at a time of manipulation input with a potential at 300 ms after the manipulation input when an operation error signal appears.

The recognizing method is not limited to the above-described two methods and some other method may be used. For example, a local maximum or a local minimum may be used, or it is possible that a maximum positive component in a waveform is detected and the amplitude thereof is compared in magnitude with a threshold value. Alternatively, an adaptive correlating filter may be used. It might be possible to provide various additional improvements in the waveform recognition method, and the recognition accuracy might be increased by, for example, combination of a pattern recognition method and a pretreatment method for an electroencephalogram signal.

As has been described, almost 90% of operation error signals can be detected, without averaging data of trials, by a method employing templates or a method in which comparison is performed for obtaining an average potential.

A first aspect of the present invention provides an operation error detection device including: an input section for receiving a manipulation input of a user; a biological signal detection section for measuring an event-related potential of electroencephalogram of the user; and an operation error judgment section for judging whether or not the manipulation input is due to an operation error of the user using the event-related potential at around 300 ms from a starting point when the input section receives the manipulation input.

A second aspect of the present invention provides the operation error detection device of the first aspect in which, if a positive component appears in part of the event-related potential located around 300 ms from the staring point, the operation error judgment section judges that the manipulation input is due to an operation error and if a positive component does not appear in the part, the operation error judgment section judges that the manipulation input is not due to an operation error.

A third aspect of the present invention provides the operation error detection device of the first aspect in which the operation error judgment section performs judgment using a signal template when an operation error occurs.

A fourth aspect of the present invention provides, as an equipment including the operation error detection device of the first aspect, an equipment including an equipment operation control section for determining an operation of the equipment based on a result of judgment by the operation error judgment section.

A fifth aspect of the present invention provides the equipment of the fourth aspect in which the equipment operation control section receives the manipulation input from the operation error judgment section and determines an operation according to the manipulation input, and when it is judged that the manipulation input is due to an operation error, the operation error judgment section stops sending the manipulation input to the equipment operation control section.

A sixth aspect of the present invention provides the equipment of the fourth aspect in which the equipment operation control section receives the manipulation input from the input section and determines an operation according to the manipulation input, and when it is judged that the manipulation input is due to an operation error, the operation error judgment section instructs the equipment operation control section to cancel the operation.

A seventh aspect of the present invention provides the equipment of the fourth aspect which further includes a correction operation determination section for determining for the manipulation input received by the input section a correction operation when the manipulation input is due to an operation error, and in which, when it is judged that the manipulation input is due to an operation error, the operation error judgment section instructs the correction operation determination section to determine a correction operation for the manipulation input and send the correction operation to the equipment operation control section.

An eighth aspect of the present invention provides the equipment of the fourth aspect in which when it is judged that the manipulation error is due to an operation error, the operation error judgment section instructs the equipment operation control section to notify a user that an operation error has been detected.

An ninth aspect of the present invention provides, as an equipment including the operation error detection device of the first aspect, an equipment including a storage section for storing the manipulation input received by the input section and a result of judgment by the operation error judgment section.

A tenth aspect of the present invention provides an operation error detection method comprising the steps of: receiving a manipulation input of a user; measuring an event-related potential of electroencephalogram of the user; and judging whether or not the manipulation input is due to an operation error of the user using the event-related potential at around 300 ms from a starting point when the input section receives the manipulation input.

An eleventh aspect of the present invention provides an equipment evaluation method including: a first step of judging using the operation error detection method of claim 10 whether or not the manipulation input to an equipment is due to an operation error; a second step of storing a result of the judgment in the first step; and a third step of evaluating operability of the equipment based on the result of the judgment stored in the second step.

Hereafter, embodiments of the present invention will be described with reference to the accompanying drawings.

FIRST EMBODIMENT

According to a first embodiment of the present invention, a biological signal of a user when the user manipulates an equipment is measured and whether or not the user's manipulation is an operation error is judged using the biological signal. An operation of the equipment is executed based on a manipulation input only when it is judged that the user's manipulation was not an operation error. Specifically, before an equipment operation is initiated, operation error judgment is performed. Then, when it is confirmed that the user's manipulation is not an operation error, the equipment is operated. Thus, an "irreversible, important equipment operation" which can not be reversed once the operation is executed or is difficult to be reversed can be automatically prevented in advance from being executed due to an operation error of the user. As specific examples of irreversible, important equipment operations are: "closing window without saving data", "overwrite saving", "deleting/overwriting video data" and the like.

FIG. 1 is a block diagram illustrating a configuration of an equipment including an operation error detection device according to this embodiment. In FIG. 1, an operation error detection device 100 is provided in an equipment 1. However, the operation error detection device 100 may be provided separately from the equipment 1.

FIG. 1 is an operation error detection device 100 includes an input section 101, a biological signal detection section 102 and an operation error judgment section 103. The input section 101 receives a manipulation input to the equipment 1 of a user 50. The biological signal detection section 102 detects a biological signal of the user 50. The operation error judgment section 103 judges from a timing, as a starting point, when the input section 101 receives the operation output of the user 50 whether or not the manipulation input is due to an operation error of the user 50 based on the biological signal of the user 50 detected by the biological signal detection section 102. An equipment operation control section 104 determines an operation of the equipment 1 based on a judgment result by the operation error judgment section 103. An output section 105 outputs a response of the equipment 1 determined by the equipment operation control section 104.

The input section 101 includes means, such as a keyboard, a mouse, a remote control, a microphone and the like, for receiving a request to the equipment 1.

The biological signal detection section 102 includes an electroencephalograph and measures as a biological signal an event-related potential in an electroencephalogram. Thus, the user 50 has to be prepared for electroencephalogram measurement, for example, by wearing an electroencephalogram or the like. An optimal electrode placing position for measuring electroencephalogram may be determined according to an experiment or the like.

The operation error judgment section 103 detects, from the electroencephalogram of the user 50 measured as a biological signal by the biological signal detection section 102, whether or not an operation error signal exists in a predetermined time range after a manipulation input is received. This detection is performed in the same manner as in the experiment method described above. For example, part of measured electroencephalogram in a range from a timing when the input section 101 receives a manipulation input to around 300 ms after the timing may be set as the predetermined time range. If a time required for operation error judgment is only about 300 ms, it is assumed that even though an equipment operation is waited until operation error judgment is performed, not much discomfort is given to the user 50 depending on a task. Moreover, judgment on whether or not the manipulation input is due to an operation error is preferably performed using a signal template at a time of operation error. In such a case, because a signal template unique to each user is created and used, a recognition rate is improved and an operation error can be detected with high accuracy. Accordingly, an equipment operation can be controlled with high accuracy and user-friendliness of the equipment is improved. As another option, in the same manner as described above, whether or not a positive component has appeared or not in part of an event-related potential of electroencephalogram at around 300 ms from a timing, as a stating point, when the input section 101 has received the manipulation input may be judged to recognize whether or not the manipulation input is due to an operation error.

The equipment operation control section 104 determines a subsequent operation of the equipment 1 based on information from the operation error judgment section 103. Specifically, the equipment operation control section 104 receives, from the operation error judgment section 103, the manipulation input which the input section 101 has received and determines an operation according to the manipulation input. When it is judged that the manipulation input is not due to an operation error, the operation error judgment section 103 sends the manipulation input received by the input section 101 as it is to the equipment operation control section 104. When it is judged that an the manipulation input is due to an operation error, the operation error judgment section 103 does not send the manipulation input received by the input section 101 to the equipment operation control section 104.

The output section 105 includes means such as a display, a speaker or the like for providing information to a user.

Figure 2:
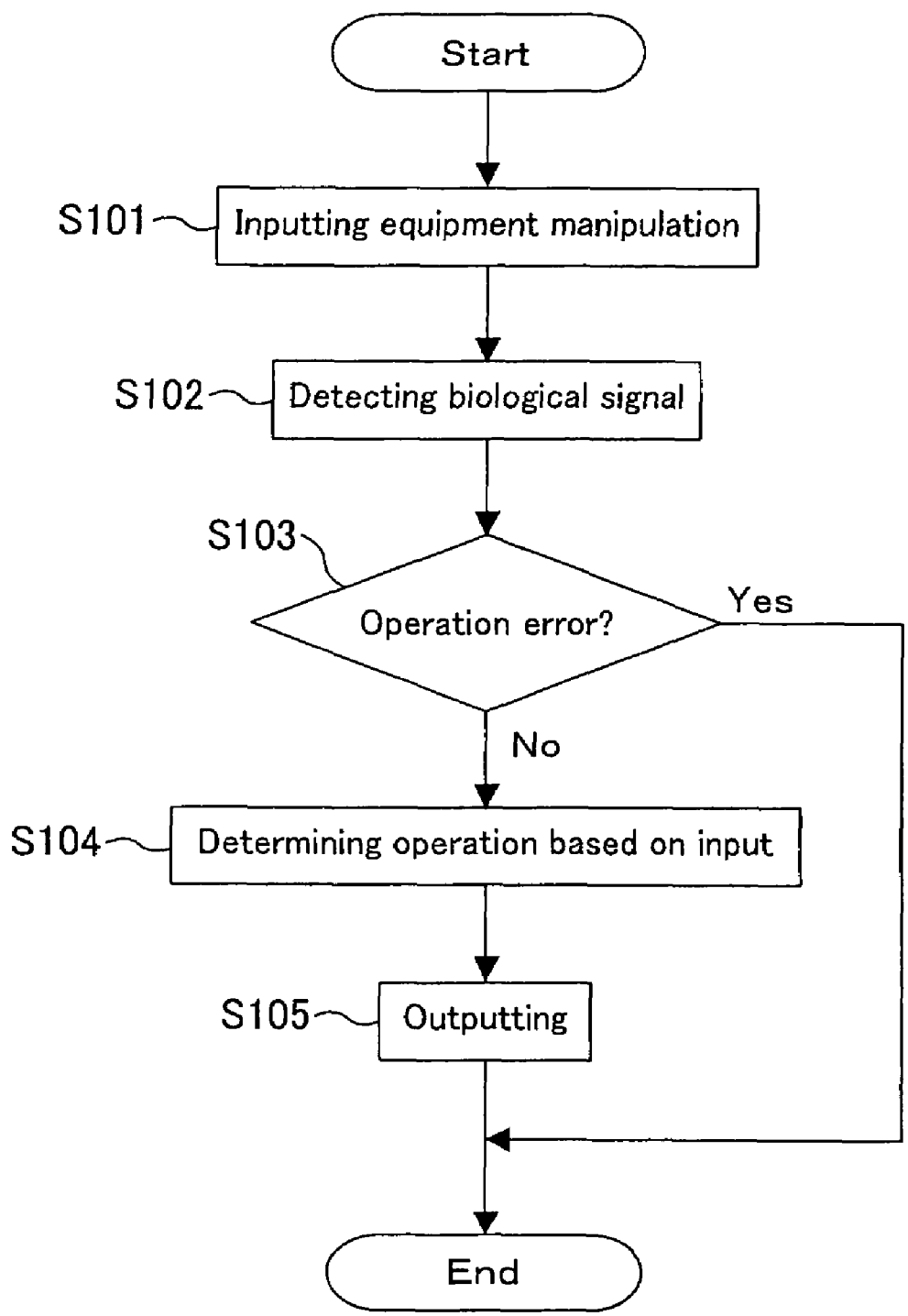
FIG. 2 is flowchart showing an operation of the configuration of FIG. 1.

The operation of the equipment 1 and the operation error detection device 100 according to this embodiment which have been formed so as to have the above-described configuration will be described using the flowchart of FIG. 2.

First, the input section 101 receives a manipulation input of the user 50 (S101). At a timing of the manipulation input in Step S101 as a starting point, the biological signal detection section 102 starts electroencephalogram measurement for obtaining an event-related potential as a biological signal of the user 50. Note that the biological signal detection section 102 may perform measurement of electroencephalogram of the user 50 at all the time and record data in a chronological order.

The operation error judgment section 103 judges whether or not the manipulation input in the Step S101 is due to an operation error based on the biological signal measured in Step S102 (S103). The judgment here is performed according to whether or not the event-related potential within a predetermined time range starting from the manipulation input of the user 50 as a starting point includes an operation error signal. When it is judged that the manipulation input is not due to an operation error (No in S103), according to an output of the operation error judgment section 103, the equipment operation control section 104 determines an equipment operation based on the manipulation input in Step S101. On the other hand, when it is judged that the manipulation input is due to an operation error (Yes in S103), the operation error judgment section 103 cancels the manipulation input and does not output the manipulation input to the equipment operation control section 104. That is, the equipment 1 does not perform an operation according to the manipulation input.

For example, when a user operating computer has performed manipulation to "close" the window which the user did not intend to close and thus did not yet save, the user would think "Oh no!" immediately after an operation error. In this case, if the computer has the same function as that of the equipment 1 of this embodiment, it is judged from the biological signal of the user that the manipulation for "close" is an operation error, and the operation of "close" can be avoided.

As described above, according to this embodiment, an irreversible operation of an equipment due to an operation error of a user can be automatically prevented from being executed.

As a known technique for preventing an irreversible operation of an equipment due to an operation error from being executed, there is a method in which a confirmation screen is displayed to confirm a user's intention as disclosed in Patent Reference 1 and Patent Reference 2. In many cases, however, a confirmation screen to be displayed includes the two common alternatives "Yes" and "No" and a user might carelessly perform wrong manipulation for confirmation. Therefore, using the technique of this embodiment also for confirmation operation of a user, execution of an irreversible operation of an equipment due to an operation error can be prevented in a double manner.

Moreover, an irreversible, important operation of an equipment may be specified and operation error judgment may be performed to the specified operation of the equipment. For example, a control system for an automobile or the like may be configured so that operation error judgment is not performed to an operation of reducing speed but performed only to an operation of increasing speed. Thus, safer driving becomes possible.

Needless to say, the above-described case in which an operation error is not executed is merely an example and various modifications can be made based on the intention of this embodiment.

SECOND EMBODIMENT

According to a second embodiment of the present invention, a biological signal of a user when the user operates an equipment is measured and whether or not manipulation of the user is an operation error is judged based on the biological signal. Then, when it is judged that the manipulation is an operation error, an equipment operation being executed based on a manipulation input is canceled. Specifically, operation error judgment is performed after the equipment operation according to the manipulation input and, when the manipulation is judged to be an operation error, the equipment operation is canceled. Thus, there is no need to force the user to perform bothering confirmation operation and correction operation, so that user-friendliness of the equipment is improved.

In the above-described first embodiment, it is first confirmed that manipulation of a user is not an operation error and then the equipment is operated. Thus, even when correct manipulation is performed, an operation of the equipment is not started until a predetermined time required for operation error judgment elapses. Accordingly, a slight time difference between manipulation input and an equipment operation is generated due to operation error judgment. In contrast, according to this embodiment, an equipment operation is started immediately after manipulation input and then operation error judgment is performed. Thus, a time difference between the manipulation input and the equipment operation is not generated. Therefore, this embodiment is more effective for an equipment operation which does not cause any trouble even though it is canceled. Specific examples of equipment operations which can be canceled later are: "forwarding/rewinding a video", "turning up/down a volume" and the like.

Figure 3:
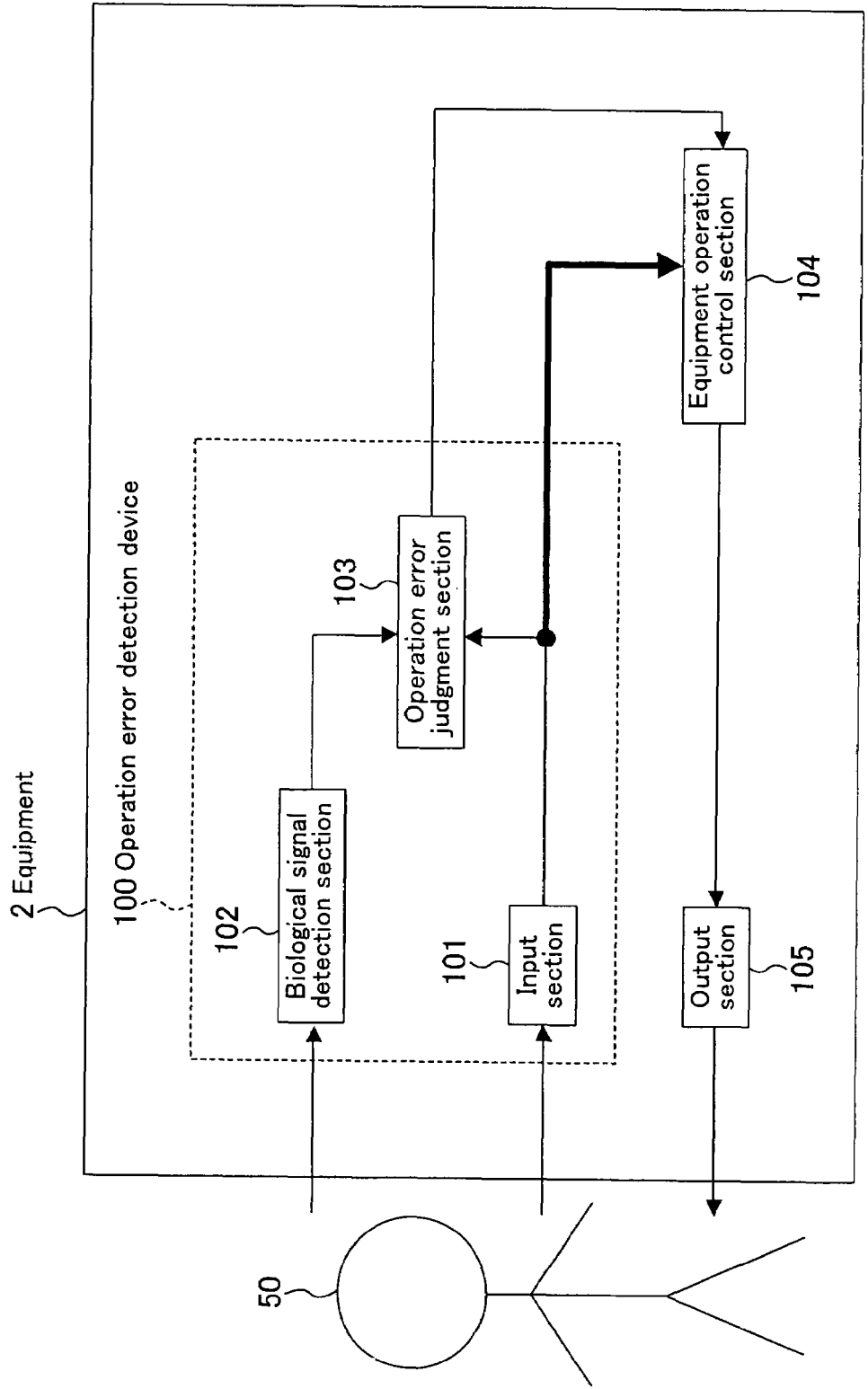
FIG. 3 is a block diagram illustrating a configuration of an equipment including an operation error detection device according to a second embodiment of the present invention.

FIG. 3 is a block diagram illustrating a configuration of an equipment including an operation error detection device according to this embodiment. In FIG. 3, each member also shown in FIG. 1 is identified by the same reference numeral and therefore the detail description thereof will be omitted. As in FIG. 1, it is assumed that an operation error detection device 100 is provided in an equipment 2. However, the operation error detection device 100 may be provided separately from the equipment 2.

In the configuration of FIG. 3, a difference from the configuration of FIG. 1 is that an input section 101 sends a received manipulation input to both of an operation error judgment section 103 and an equipment operation control section 104. Specifically, the equipment operation control section 104 receives a manipulation input from the input section 101 and determines an operation according to the manipulation input. When it is judged that the manipulation input of the user 50 is due to an operation error, the operation error judgment section 103 instructs the equipment operation control section 104 to cancel the determined operation.

Figure 4:
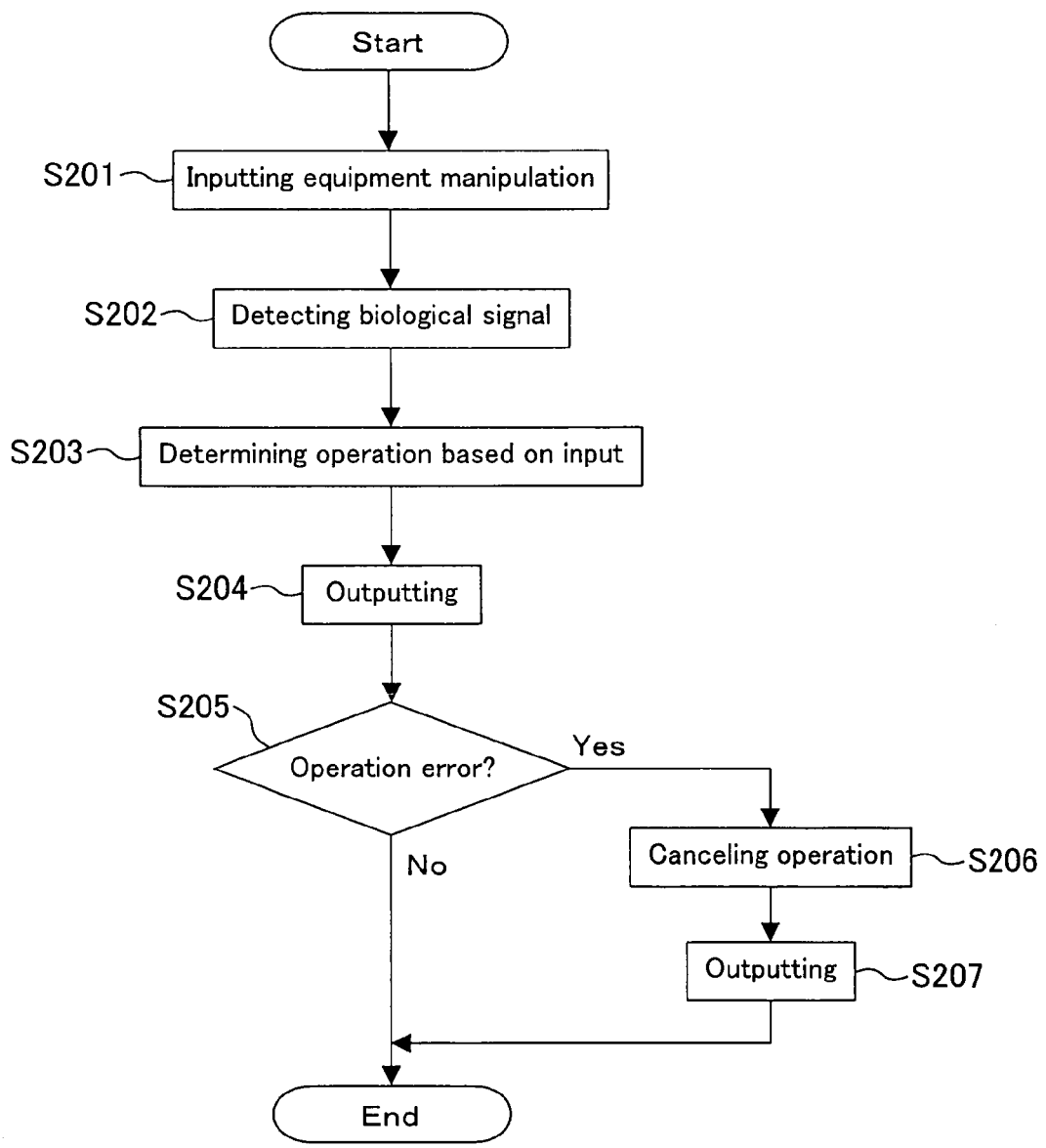
FIG. 4 is flowchart showing an operation of the configuration of FIG. 3.

The operation of the equipment 2 and the operation error detection device 100 which have been formed so as to have the above-described configuration will be described using the flowchart of FIG. 4.

First, the input section 101 receives a manipulation input of the user 50 (S201). At a timing of the manipulation input in Step S201 as a starting point, the biological signal detection section 102 starts electroencephalogram measurement for obtaining an event-related potential as a biological signal of the user 50 (S202). Note that the biological signal detection section 102 may perform measurement of electroencephalogram of the user 50 at all the time and record data in a chronological order.

The equipment operation control section 104 receives the manipulation input in Step S201 from the input section 101 and determines an equipment operation according to the manipulation input (S203). The output section 105 outputs the determined equipment operation (S204). Thereafter, the operation error judgment section 103 judges, based on the biological signal measured in Step S202, whether or not the manipulation input in Step S201 is due to an operation error (S205). The judgment here is performed according to whether or not the event-related potential within a predetermined time range starting from the manipulation input of the user 50 as a starting point includes an operation error signal. When it is judged that the manipulation input is due to an operation error (Yes in S205), the operation error judgment section 103 instructs the equipment operation control section 104 to cancel the operation and in response to the instruction, the equipment operation control section 104 cancels the operation determined in the Step S203 (S206). The output section 105 outputs so that a state of the equipment 2 returns a previous state before receiving the manipulation input in S201. On the other hand, when it is judged that the manipulation input is not due to an operation error (No in S205), the output performed in Step S204 is continuously performed.

For example, in the case of operating a video machine, when a user wants to perform a "forward" or "rewind" operation and correctly presses an assumed "forward" or "rewind" button, the video machine is operated as the user intended.

However, when a user wants to perform a "forward" operation but presses the "rewind" button, the user notices his/her operation error right after pressing the wrong button and would think "Oh no!" In comparison to the above-described experiment, L and R corresponds to the intended "forward" and "rewind" operations, respectively, and the left and right buttons of the mouse corresponds to the "forward" button and the "rewind" button, respectively.

According to this embodiment, for example, in the case where a user wants to "forward" a video in a reproduction state and performs manipulation, when the user mistakenly presses the "rewind" button and notices an operation error immediately after the manipulation, the mistake can be detected by an operation error signal. Thus, the equipment 2 can cancel an operation error, i.e., "rewind" and return the video to the previous reproduction state. In the same manner, the operation of increasing/reducing a volume can be canceled according to detection of an operation error.

As described above, according to this embodiment, an equipment judges whether or not a manipulation input of a user is due to an operation error. When it is judged that the manipulation input is due to an operation error, an operation according to the manipulation input is canceled and the equipment is returned to a previous state before receiving the manipulation input. Thus, the user is not forced to perform a bothering correction operation and a smooth an equipment operation is possible. Moreover, a time difference due to operation error judgment is not generated between the manipulation error and the equipment operation. Accordingly, when the manipulation is correct, a highly responsive operation is performed.

The above-described case in which an equipment operation is canceled is merely an example and various modifications can be made based on the intention of this embodiment in which an operation error of a user is detected and an equipment operation according to the operation error is canceled.

According to this embodiment, when the manipulation input is due to an operation error, an equipment operation is canceled. With or instead of this cancellation operation, it may be notified to the user 50 itself that an operation error has been detected. Specifically, when it is judged that the manipulation input is due to an operation error, the operation error judgment section 103 instructs the equipment operation control section 104 to notify the user 50 that the operation error has been detected through a speaker or the like. Thus, it is possible to make the user 50 recognize the operation error again.

Moreover, it may be notified to some other user than the user 50 that the operation error has been detected. For example, when a user has mistakenly sent a mail, it is notified to a receiver of the mail that the mail is sent due to an operation error. Thus, people around the user can recognize the operation error and can deal with the operation error.

Moreover, the degree of importance of a manipulation input of a user may be judged. Then, according to the judged degree of importance, the processing shown in the first embodiment and the processing shown in the second embodiment may be switched and executed. Specifically, as described in the first embodiment, an irreversible equipment operation may be executed after a result of operation error judgment has been waited, so that an equipment operation can be prevented from happening. On the other hand, as described in the second embodiment, an equipment operation which can be canceled layer may be executed without a time difference and may be canceled after it is judged that the manipulation input of the user is due to an operation error. Thus, the advantage of the first embodiment that an operation error of an important equipment operation can be prevented from happening and the advantage of the second embodiment that an operation error can be canceled with high operability can be achieved.

Figure 5:
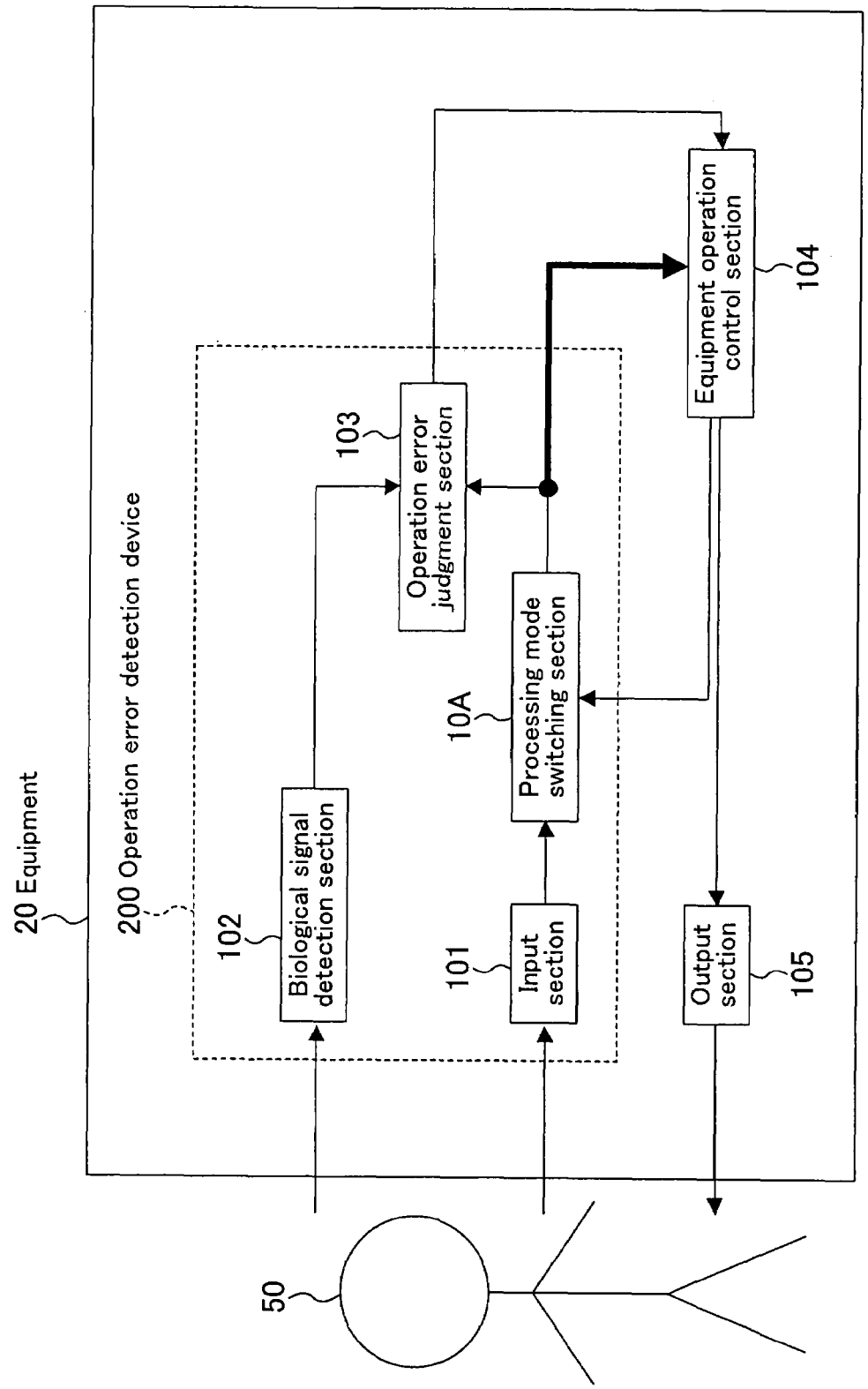
FIG. 5 is a block diagram illustrating a configuration obtained by combination of the first embodiment and the second embodiment.

FIG. 5 is a block diagram illustrating a configuration of an equipment for switching processing according to a manipulation input in the above-described manner. In FIG. 5, each member also shown in FIG. 1 and FIG. 3 is identified by the same reference numeral and therefore the description thereof will be omitted.

In the configuration shown in FIG. 5, an operation error detection device 200 includes a processing mode switching section 10A as well as an input section 101, a biological signal detection section 102 and an operation error judgment section 103. The processing mode switching section 10A receives a state of an equipment operation obtained from an equipment operation control section 104 and a manipulation input of a user from the input section 101, judges the degree of importance of the manipulation input of the user according to the state of the equipment operation and the manipulation input and changes subsequent processing mode. For example, in computer operation, the degree of importance of an "OK" button to be selected in a pop-up screen for "Usage explanation" is set to be low and the degree of importance of an "OK" button to be selected at a screen of "Close window without saving" is set to be high. In this manner, the degree of importance of operation is judged by setting the degree of importance of a subsequent manipulation input beforehand for each state of operation of the equipment. When the degree of an operation can be judged from a manipulation input of the user 50 (For example, when an operation of a "Decide" button is to be judged to be important), the state of the equipment operation does not have to be obtained from the equipment operation control section 104.

Figure 6:
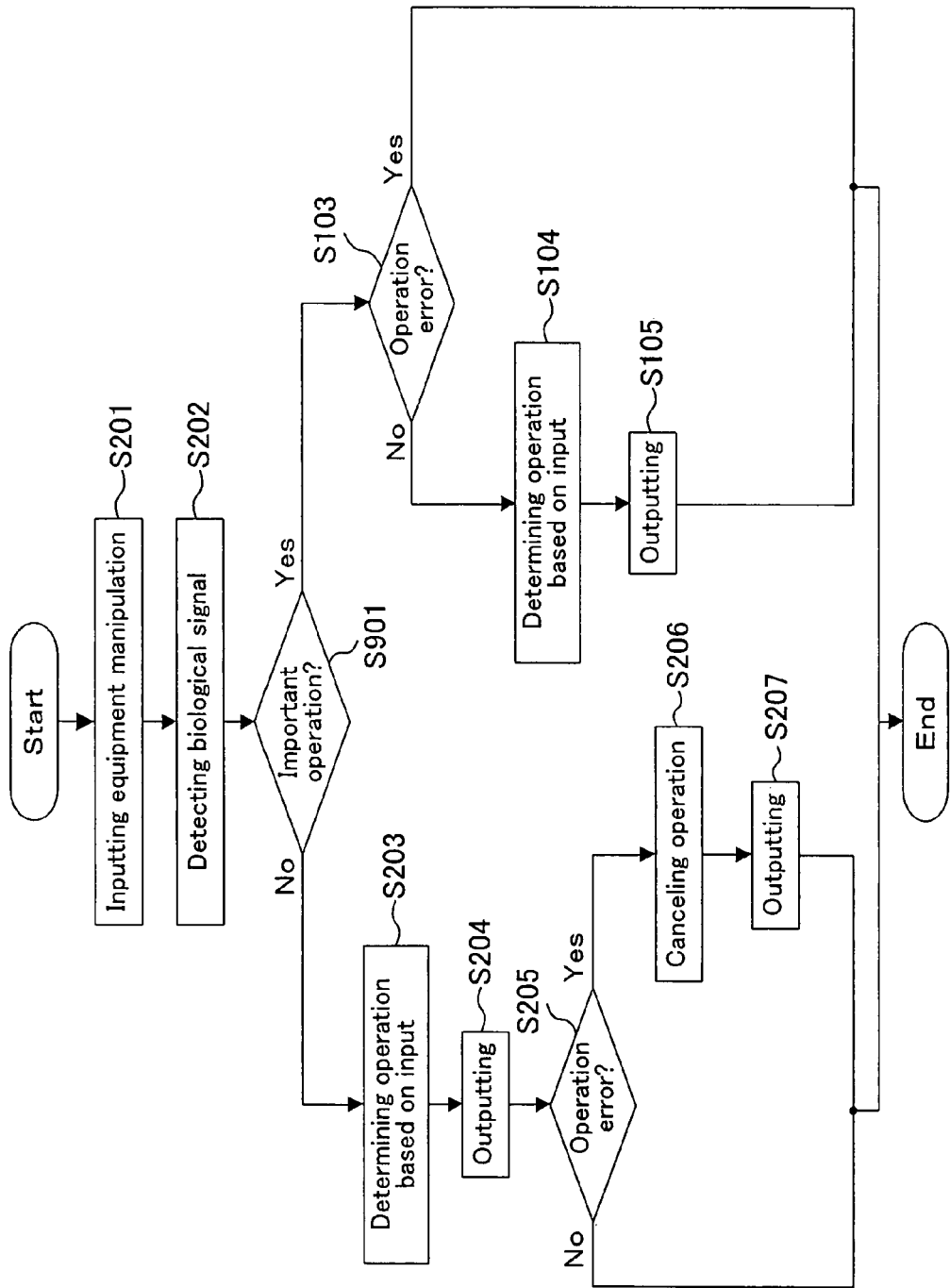
FIG. 6 is a flowchart showing an operation of the configuration of FIG. 5.

The operation of the hard mask formation film 20 and the operation error detection device 200 which have been formed so as to have the configuration of FIG. 5 will be described using the flowchart of FIG. 6. In FIG. 6, each step also shown in FIG. 2 and FIG. 4 is identified by the same reference numeral and therefore the description thereof will be omitted.

First, the input section 101 receives a manipulation input of the user 50 (S201) and the biological signal detection section 102 obtains an event-related potential as a biological signal of the user 50 (S202). In Step S901, the processing mode switching section 10A judges the degree of importance of the manipulation input which has been received in Step S201 according to a state of an equipment operation obtained from the equipment operation control section 104 and the like.

When it is judged that the manipulation input is important (Yes in S901), the process proceeds to Step S103 and then the same operation as the subsequent steps including S103 of the first embodiment is performed. On the other hand, when it is judged that the manipulation input is not important (No in S901), the process proceeds to Step S203 and then the same operation in the subsequent steps including S203 of the second embodiment is performed.

FIGS. 7(*a*) and 7(*b*) are conceptual diagram and table showing timing for operation according to the procedure shown in FIG. 6. In FIG. 7(*a*), the degree of importance of the manipulation input is judged at t=0. When it is judged that the manipulation input is not important, at an operation timing (1) (t=Δ), a corresponding operation is executed with substantially no time difference. Note that in FIG. 7(*a*) and FIG. 7(*b*), Δ indicates a predetermined time required for executing an operation. Thereafter, when it is judged that the manipulation input is due to an operation error, at an operation timing (2)

Figures 7A, 7B:
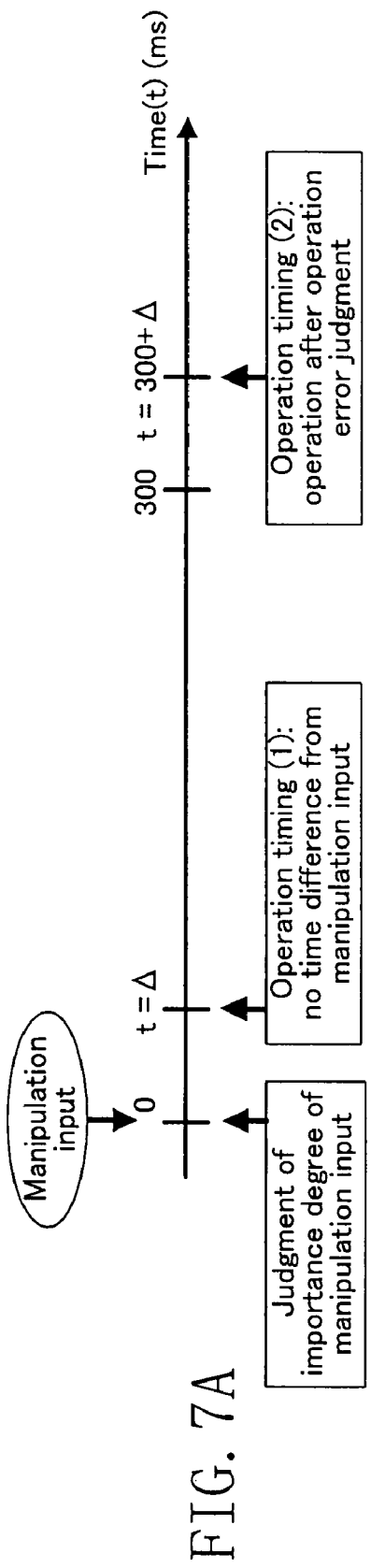
FIGS. 7(a) and 7(b) are conceptual diagram and table showing timing for operation according to the flow of FIG. 6.

(t=300+Δ where operation error judgment requires 300 ms), the operation executed at the operation timing (1) is canceled. On the other hand, when it is judged at t=0 that the manipulation input is not due to an operation error, at the operation timing (2), it is confirmed that the manipulation input is not due to an operation error and then a corresponding operation is executed. FIG. 7(b) shows the relationship between the degree of importance of a manipulation input and each of an equipment operation and timing of canceling operation.

As described above, the degree of importance of a manipulation input of a user is judged and, based on a result of the judgment, a processing method is changed. Thus, for example, an unimportant operation such as "rewind" and the like can be executed with no time difference. On the other hand, execution of an irreversible, important equipment operation such as "deleting/overwriting recorded video" and the like can be waited until a result of operation error judgment is obtained and then performed. Specifically, an irreversible equipment operation due to an operation error can be canceled before happening by judging the degree of importance of the manipulation input, and an operation delay due to an operation error judgment time can be eliminated by immediately executing processing of an unimportant operation. Therefore, a highly reliable equipment with high operability can be achieved.

THIRD EMBODIMENT

According to a third embodiment of the present invention, a biological signal of a user when the user operates an equipment is measured and whether or not manipulation of the user is an operation error is judged based on the biological signal. Then, when it is judged that the manipulation is an operation error, a correction operation is estimated and an equipment operation of the operation error is corrected. Thus, the user does not have to correct the operation error and user friendliness of the equipment is improved. An operation that the user intended is not corrected even though it seems like an operation error, and thus, as in a known technique, an automatic correction that the user does not desire is not performed.

Figure 8:
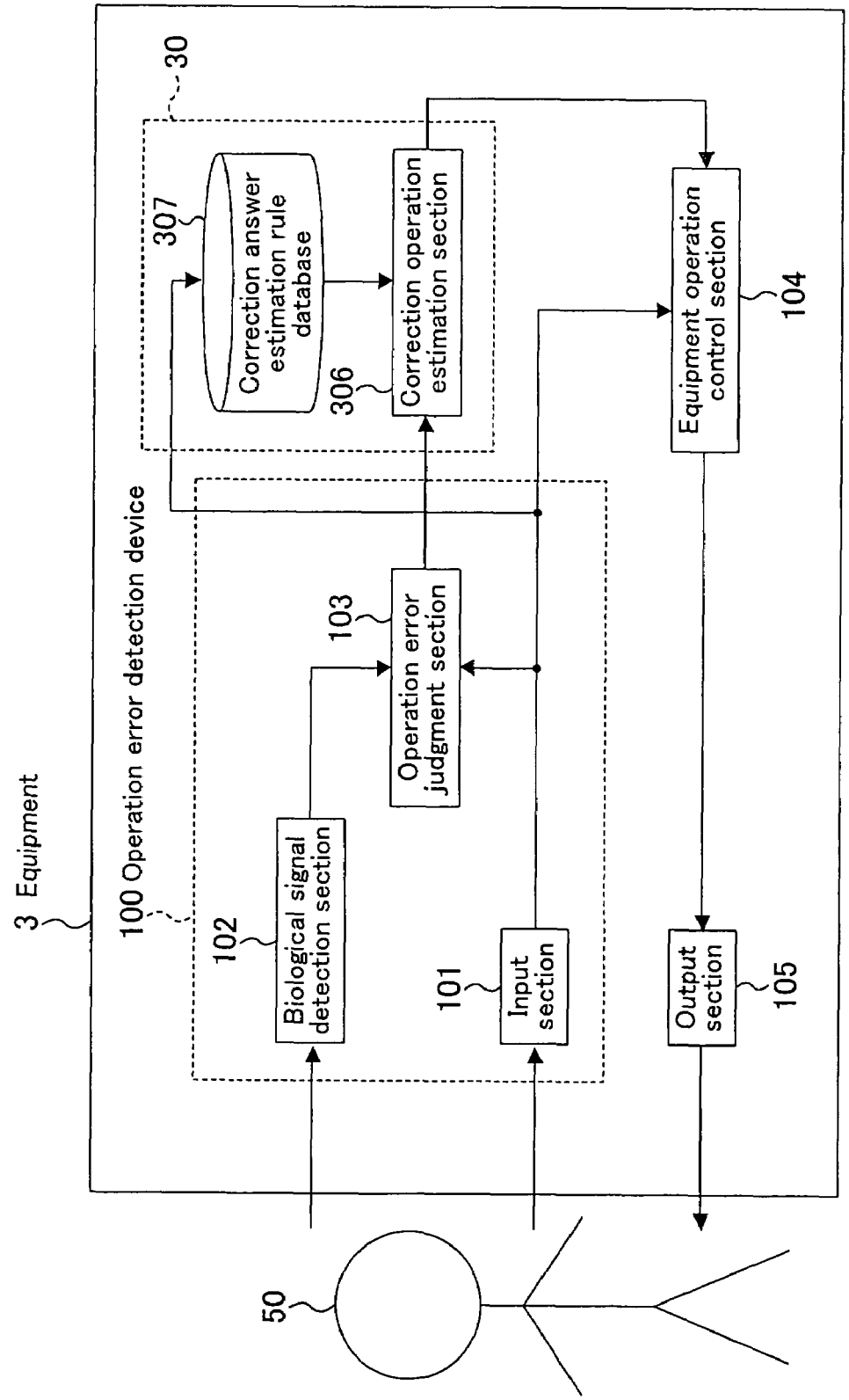
FIG. 8 is a block diagram illustrating a configuration of an equipment including an operation error detection device according to a third embodiment of the present invention.

FIG. 8 is a block diagram illustrating a configuration of an equipment including an operation error detection device according to this embodiment. In FIG. 8, each member also shown in FIG. 1 is identified by the same reference numeral and therefore the detail description thereof will be omitted. As in FIG. 1, in FIG. 8, an operation error detection device 100 is provided in an equipment 3. However, the operation error detection device 100 may be provided separately from the equipment 3.

In the configuration of FIG. 8, a difference from the configuration of FIG. 3 is that a correction operation determination section 30 including a correction operation estimation section 306 and a correction answer estimation rule database 307 is provided therein. The correction operation determination section 30 determines a correction operation for a manipulation input received by an input section 101 when it is judged that the manipulation input is an operation error. When it is judged that the manipulation input received by the input section 101 is due to an operation error, the operation error judgment section 103 instructs the correction operation determination section 30 to determine a correction operation for the manipulation input and send the correction operation to the equipment operation control section 104.

FIG. 9 is a table showing exemplary data stored in the correction answer estimation rule database 307. In this case, the equipment 3 of FIG. 8 includes a word-processing function. As shown in FIG. 9, for example, "about a" is stored as a correction answer for a manipulation input "about a". The correction operation estimation section 306 receives an instruction from the operation error judgment section 103, refers the correction answer estimation rule database 307 and estimates a correction operation to the manipulation input received by the input section 101. Note that the contents of the correction answer estimation rule database 307 may be updated, based on an operation input received by the input section 101 and a result of operation error judgment by the operation error judgment section 103, according to the pattern of typing errors made by a user.

Figure 10:
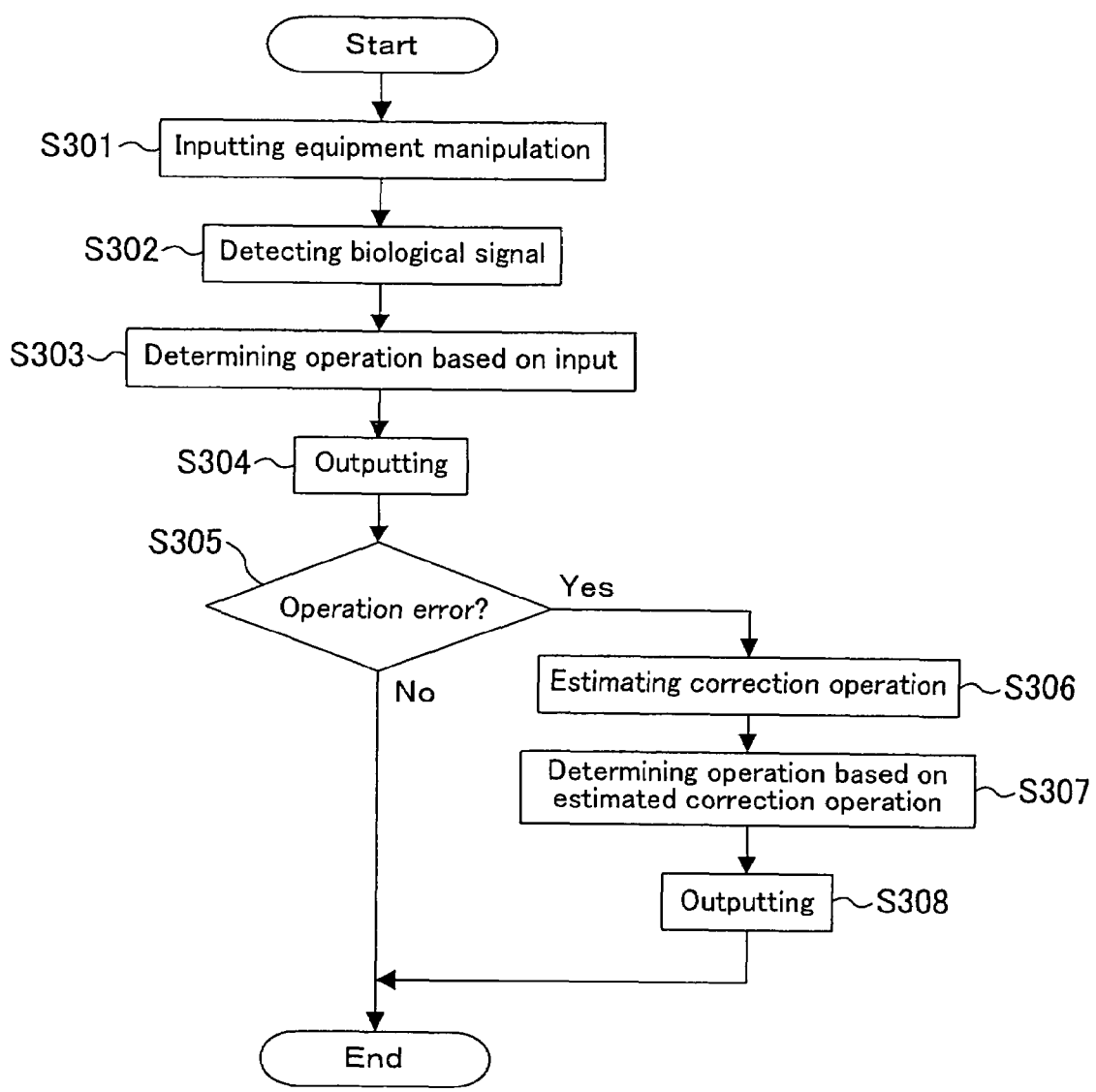
FIG. 10 is a flowchart showing an operation of the configuration of FIG. 8.

The operation of the equipment 3 and the operation error detection device 100 according to this embodiment which have been formed so as to have the above-described configuration will be described using the flowchart of FIG. 10.

First, the input section 101 receives a manipulation input of the user 50 (S301). The biological signal detection section 102 starts electroencephalogram measurement at a timing of an manipulation input in Step S301 as a starting point so as to obtain an event-related potential as a biological signal of the user 50 (S302). The biological signal detection section 102 may perform measurement of electroencephalogram of the user 50 at all the time and record data in a chronological order. The equipment operation control section 104 receives a manipulation input in Step S301 from the input section 101 and determines an equipment operation according to the manipulation input (S303). Then, the output section 105 outputs the determined equipment operation (S304). Thereafter, the operation error judgment section 103 judges whether or not the manipulation input in Step S301 is due to an operation error based on the biological signal measured in Step S302 (S305). The judgment here is performed according to whether or not the event-related potential within a predetermined time range from the manipulation input of the user 50 as a starting point includes an operation error signal. The above-described operation till Step S305 is performed in the same manner as in Steps S201 through S205 of FIG. 4 in the second embodiment.

When it is judged that the manipulation input is due to an operation error (Yes in S305), to execute correction for the manipulation input received in Step S301, The correction operation estimation section 306 estimates a correction operation for the manipulation input based on the correction answer estimation rule database 307 (S306). The estimated correction operation is sent to the equipment operation control section 104. The equipment operation control section 104 determines an operation according to the correction operation and corrects the equipment operation determined in Step S303 (S307). The output section 105 outputs a correction operation determined in Step S307. On the other hand, when it is judged that the manipulation input is not due to an operation error (No in S305), the output performed by the output section 105 in Step S304 is continued.

For example, there already exists a system for correcting a typing error made when performing keyboard input. In such a system, however, in the case where a correction pattern shown in FIG. 9 is given beforehand, even if a user intentionally typed "hge", "hge" is judged to be a typing error and automatically corrected to "he".

In many cases, if a user made a typing error, the user would feel "Oh no!" immediately after he/she typed and notice even before a result of the typing error is displayed in the screen. Therefore, according to this embodiment, only an unintentional input, i.e., a typing error due to an operation error can be automatically corrected. Moreover, it is possible to specify a place of a typing error within a time period of about 300 ms in which operation error judgment is performed. Thus, unnecessary correction is not performed and the user can type as he/she wants. Furthermore, a tying error due to an operation error is automatically corrected, so that a correction operation is not necessary and user friendliness of the equipment is largely improved.

The above-described case of operation correction is merely an example and various modifications can be made based on the intention of this embodiment in which an operation error of a user is detected and the operation error is corrected.

FOURTH EMBODIMENT

According to a fourth embodiment of the present invention, a biological signal of a user when the user operates an equipment is measured, whether or not manipulation of the user is an operation error is judged based on the biological signal and operation input information and error operation judgment result information are stored in database. Then, based on stored data, operability evaluation for the equipment is performed. In a known technique, when there is a mistake in manipulation, it has been not possible to judge which the mistake is due to an operation error or due to lack of understanding of how to manipulate the equipment. In contrast, according to this embodiment, a mistake due to an operation error, such as pressing a wrong button or the like can be identify from various mistakes in manipulation, so that more detail usability evaluation becomes possible.

Figure 11:
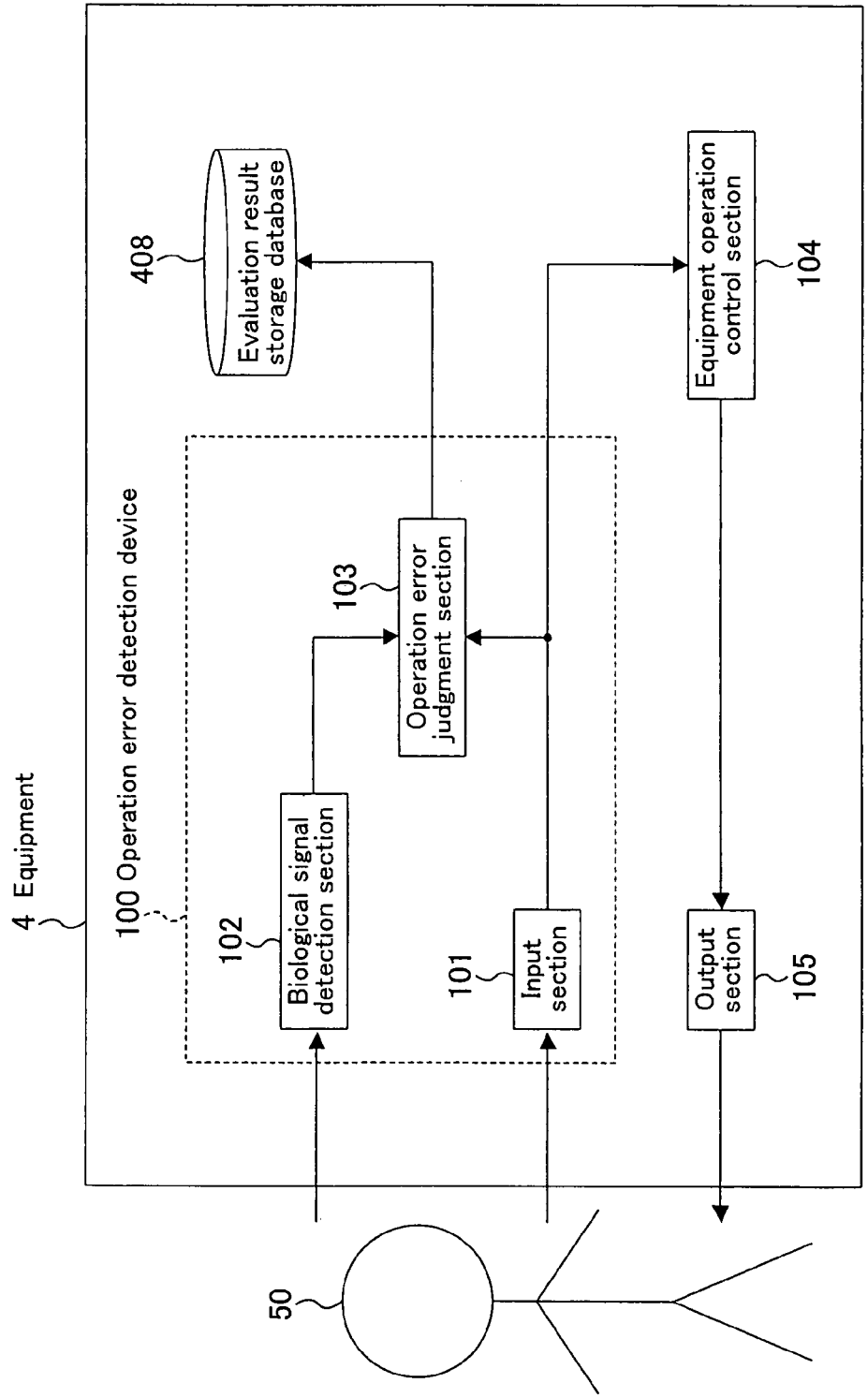
FIG. 11 is a block diagram illustrating a configuration of an equipment including an operation error detection device according to a fourth embodiment of the present invention.

FIG. 11 is a block diagram illustrating a configuration of an equipment including an operation error detection device according to this embodiment. In FIG. 11, each member also shown in FIG. 1 is identified by the same reference numeral and therefore the detail description thereof will be omitted. As in FIG. 1, it is assumed that an operation error detection device 100 is provided in an equipment 4. However, the operation error detection device 100 may be provided separately from the equipment 4.

In the configuration of FIG. 11, a difference from the configuration of FIG. 3 is that an evaluation result storage database 408 as a storage section for storing a manipulation input received by an input section 101 and a result of judgment by a operation error judgment section 103 is provided therein. The evaluation result storage database 408 performs, for each type of equipment operations performed by a user 50, counting on whether or not the user 50 has performed an operation error and storing the count. Moreover, in the configuration of FIG. 11, an output operation to an equipment operation control section 104 from an equipment operation control section 104 are omitted. Note that the output operation does not have to be omitted.

Figure 12:
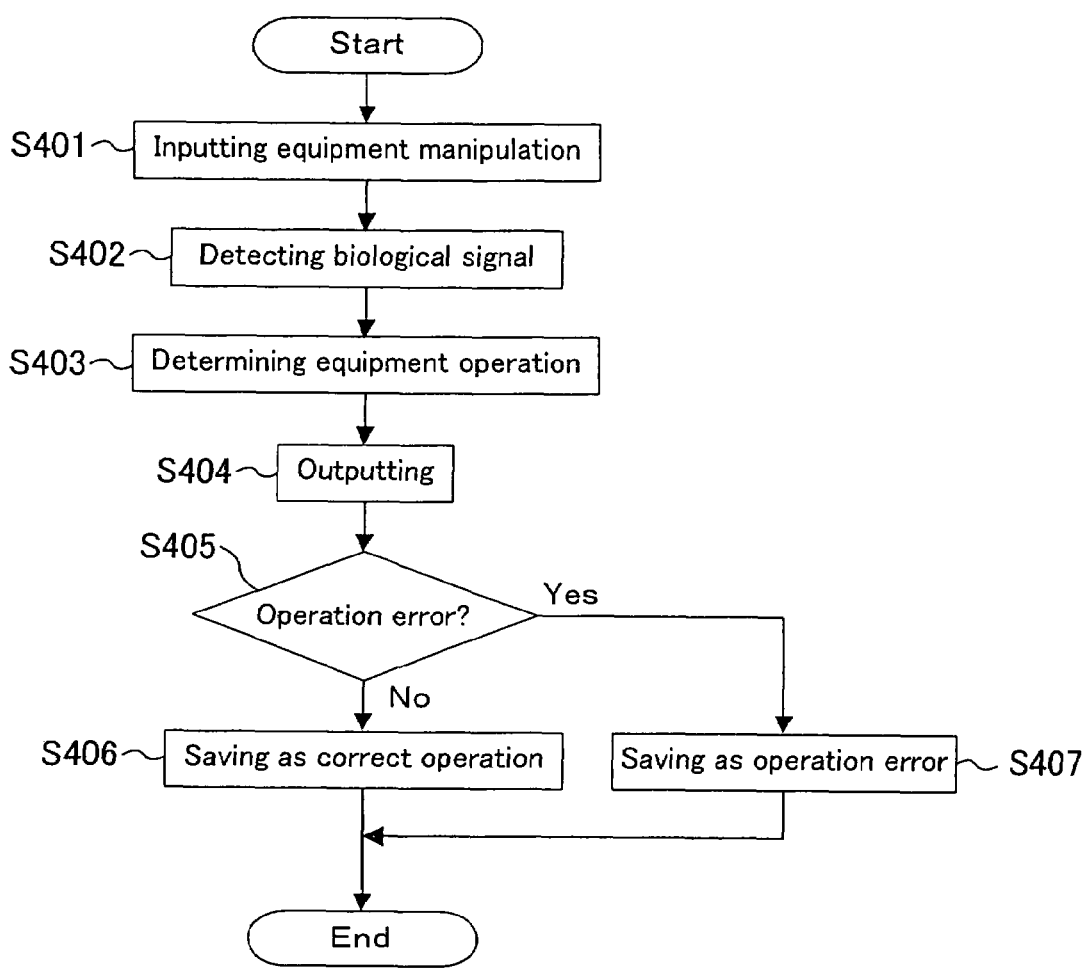
FIG. 12 is a flowchart showing an operation of the configuration of FIG. 11.

The operation of the equipment 4 and the operation error detection device 100 according to this embodiment which have been formed so as to have the configuration of FIG. 11 will be described using the flowchart of FIG. 12.

First, the input section 101 receives a manipulation input of the user 50 (S401). The biological signal detection section 102 starts electroencephalogram measurement at a timing of an manipulation input in Step S401 as a starting point so as to obtain an event-related potential as a biological signal of the user 50 (S402). The biological signal detection section 102 may perform measurement of electroencephalogram of the user 50 at all the time and record data in a chronological order. The equipment operation control section 104 receives a manipulation input in Step S401 from the input section 101 and determines an equipment operation according to the manipulation input (S403). Then, the output section 105 outputs the determined equipment operation (S404). Thereafter, the operation error judgment section 103 judges whether or not the manipulation input in Step S401 is due to an operation error, based on the biological signal measured in Step S402 (S405). The judgment here is performed according to whether or not the event-related potential within a predetermined time range from the manipulation input of the user 50 as a starting point includes an operation error signal. The above-described operation till Step S405 is performed in the same manner as in Steps S201 through S205 of FIG. 4 in the second embodiment.

When it is judged that the manipulation input is not due to an operation error (No in S405), the operation input in Step S401 and the statement that the manipulation input is a correct manipulation are stored in the evaluation result storage database 408 (S406). On the other hand, when it is judged that the manipulation input is due to an operation error (Yes in S405), the operation input in S401 and the statement that the manipulation input is an operation error are stored in the evaluation result storage database 408 (S407).

Based on data stored in the evaluation result storage database 408, evaluation of operability and the like of the equipment 4 is performed.

The effectiveness of operability evaluation according to this embodiment will be described with reference to FIG. 13 and FIG. 14. FIG. 13 is a table showing an example of results of operability evaluation by a known method. FIG. 14 is a table showing an example of results of operability evaluation according to this embodiment.

For example, when operation evaluation is performed for an operation button, in the known technique, as shown in FIG. 13, the operability can be evaluated only according to a percentage of mistake in manipulation for each button. In this case, according to the evaluation result of FIG. 13, for each of a button A and a button B, a manipulation mistake has occurred at a probability of 20%, so that evaluations of the button A and the button B are the same.

In contrast, according to this embodiment, as shown in FIG. 14, not only the mere percentage of mistakes in manipulation but a percentage of an operation error such as pressing a wrong button, e.g., the case where "a user pressed a different button from a button which the user intended to press" can be obtained. In such a case, according to an evaluation result shown in FIG. 14, the operation error percentages for the button A and the button B are 2% and 18%, respectively, are very different from each other. Thus, in contrast to the known method in which the same evaluation results are obtained for the button A and the button B, it can be further recognized that the reason why a mistake in manipulation of the button A occurs is that a correct manipulation was not understood and the reason why a mistake in manipulation of the button B occurs is that it is difficult to press the button B even if a correct manipulation was understood. That is, even similar mistakes in manipulation can be distinguished between a mistake due to lack of user's understanding and a mistake due to operability of an equipment. Thus, improvement strategies can be determined for each means of an interface, such as a button and the like.

As has been described, according to this embodiment, operation error judgment is performed and a result of the judgment is stored. Thus, accuracy of usability evaluation can be improved.

Moreover, whether or not manipulation of a user is an operation error and whether or not an operation error signal is detected may be stored for each type of equipment operations and evaluation of equipment usability may be performed for each equipment operation, based on a result of the stored information. Thus, usability evaluation of not entire equipment but each function of the equipment can be conducted by a large number of users. Moreover, this embodiment can be applied to evaluation of usability for each of user groups, such as senior users and young users, having a certain attribute and can be reflected to improvement of equipment design and the new equipment design.

INDUSTRIAL APPLICABILITY

According to the present invention, an operation error of a user can be directly detected. Therefore, the present invention is useful in improving operability of an information terminal and the like. Moreover, a state where an operation error occurs is stored and the stored state can be used in evaluation of operability of an equipment.

The invention claimed is:

1. An operation error detection device comprising:
   an input section for receiving a manipulation input of a user;
   a biological signal detection section for measuring an event-related potential of electroencephalogram of the user; and
   an operation error judgment section for judging whether or not the manipulation input is due to an operation error of the user using the event-related potential at around 300 ms from a starting point when the input section receives the manipulation input,
   wherein if a positive component appears in part of the event-related potential located around 300 ms from the starting point, the operation error judgment section judges that the manipulation input is due to an operation error and if a positive component does not appear in the part, the operation error judgment section judges that the manipulation input is not due to an operation error.

2. The operation error detection device of claim 1, wherein the operation error judgment section performs judgment using a signal template when an operation error occurs.

3. An equipment including the operation error detection device of claim 1, the equipment comprising: an equipment operation control section for determining an operation of the equipment based on a result of judgment by the operation error judgment section.

4. The equipment of claim 3, wherein the equipment operation control section receives the manipulation input from the operation error judgment section and determines an operation according to the manipulation input, and
   when it is judged that the manipulation input is due to an operation error, the operation error judgment section stops sending the manipulation input to the equipment operation control section.

5. The equipment of claim 3, wherein the equipment operation control section receives the manipulation input from the input section and determines an operation according to the manipulation input, and
   when it is judged that the manipulation input is due to an operation error, the operation error judgment section instructs the equipment operation control section to cancel the operation.

6. The equipment of claim 3, further comprising a correction operation determination section for determining for the manipulation input received by the input section a correction operation when the manipulation input is due to an operation error,
   wherein when it is judged that the manipulation input is due to an operation error, the operation error judgment section instructs the correction operation determination section to determine a correction operation for the manipulation input and send the correction operation to the equipment operation control section.

7. The equipment of claim 3, wherein when it is judged that the manipulation error is due to an operation error, the operation error judgment section instructs the equipment operation control section to notify a user that an operation error has been detected.

8. An equipment including the operation error detection device of claim 1, comprising a storage section for storing the manipulation input received by the input section and a result of judgment by the operation error judgment section.

9. An operation error detection method comprising the steps of:
   receiving a manipulation input of a user;
   measuring an event-related potential of electroencephalogram of the user; and
   judging whether or not the manipulation input is due to an operation error of the user using the event-related potential at around 300 ms from a starting point when the input section receives the manipulation input,
   wherein at the judging step, if a positive component appears in part of the event-related potential located around 300 ms from the starting point, it is judged that the manipulation input is due to an operation error and if a positive component does not appear in the part, it is judged that the manipulation input is not due to an operation error.

10. An equipment evaluation method comprising:
    a first step of judging using the operation error detection method of claim 9 whether or not the manipulation input to an equipment is due to an operation error;
    a second step of storing a result of the judgment in the first step; and
    a third step of evaluating operability of the equipment based on the result of the judgment stored in the second step.

* * * * *